(12) United States Patent
Stanish et al.

(10) Patent No.: US 6,308,571 B1
(45) Date of Patent: *Oct. 30, 2001

(54) METHOD FOR DETERMINING CROOK POTENTIAL IN WOOD

(75) Inventors: Mark A. Stanish, Seattle; Stan L. Floyd, Enumclaw, both of WA (US); Steven M. Cramer, Lodi, WI (US)

(73) Assignee: Weyerhaeuser Company, Federal Way, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/388,192

(22) Filed: Sep. 1, 1999

Related U.S. Application Data

(60) Provisional application No. 60/098,980, filed on Sep. 2, 1998.

(51) Int. Cl.[7] ............................ G01N 29/18; F26B 13/10
(52) U.S. Cl. ................... 73/597; 73/601; 73/624; 73/432.1; 324/639; 324/663; 702/38; 702/39; 702/40; 702/153; 250/330; 250/341.1; 250/359.1; 144/356; 144/357; 83/73; 83/361; 83/365; 83/371; 356/364
(58) Field of Search ........................ 73/597, 601, 624, 73/627, 628, 73, 75, 159, 160, 432.1; 324/637–640, 663–664, 683–684, 686–690; 356/364, 371, 376, 383, 384, 445, 446–448, 237, 239; 250/330, 338.1, 341.1, 340, 341.6, 341.8, 358.1, 359.1, 360.1; 144/356, 357, 380; 83/69–73, 360–361, 365, 370, 371; 364/474.13, 474.09, 478.01; 702/35, 38–40, 81, 179–180, 181, 189, 196, 126, 134, 135, 136, 155

(56) References Cited

U.S. PATENT DOCUMENTS 3,664,180   5/1972   McDonald et al. .................. 73/67.6

(List continued on next page.)

OTHER PUBLICATIONS

Simpson, William T., et al., "Mechanism of Crook Development in Lumber During Drying", Wood and Fiber Science, 16(4), (Oct. 1984), pp. 523–536.*

(List continued on next page.)

Primary Examiner—Hezron Williams
Assistant Examiner—Rose M. Miller
(74) Attorney, Agent, or Firm—Klarquist Sparkman Campbell Leigh & Whinston, LLP

(57) ABSTRACT

A method for determining crook potential of wood is described. One embodiment comprises nondestructively obtaining lengthwise shrinkage rates (from a third party or by direct measurement) of wood and then determining crook potential of the wood based on the lengthwise shrinkage rates. Where the wood comprises lumber, lengthwise shrinkage rate measurements typically are made on at least one major planar surface of the lumber. The method typically comprises determining lengthwise shrinkage rates two or more measuring points separated by a predetermined distance, such as at substantially one-foot intervals along the lumber. Particular embodiments of the present invention determine lengthwise shrinkage rates using infrared radiation, microwave radiation, electricity, ultrasound energy, and combinations thereof Working embodiments of the method use ultrasound energy to determine lengthwise shrinkage rates. For example, one working embodiment measures the speed of an ultrasound pulse through wood to determine the modulus of elasticity (MOE) of the wood which can then be correlated to the lengthwise shrinkage rate. In another example, lengthwise shrinkage rate can be determined from the speed of an ultrasound pulse using an empirically derived formula, such as an exponential formula. Another embodiment of the present invention comprises determining crook potential of wood based on non-averaged lengthwise shrinkage rates. Another embodiment of the present invention comprises determining crook potential is determined using a finite element model (FEM). The method the present invention provides can determine crook potential that correlates with actual measured crook with an $R^2$ value of at least 0.5.

66 Claims, 24 Drawing Sheets

U.S. PATENT DOCUMENTS

| | | | | |
|---|---|---|---|---|
| 3,805,156 | | 4/1974 | Norton et al. ...................... | 324/61 R |
| 4,201,093 | * | 5/1980 | Logan .................................... | 73/618 |
| 4,500,835 | | 2/1985 | Heikkila .......................... | 324/585 R |
| 4,538,656 | * | 9/1985 | Wiklund ............................... | 144/378 |
| 4,606,645 | | 8/1986 | Matthews et al. .................. | 356/446 |
| 4,852,029 | * | 7/1989 | Pope et al. ........................... | 364/556 |
| 4,916,629 | | 4/1990 | Bogue et al. ........................ | 364/507 |
| 4,926,350 | | 5/1990 | Bechtel et al. ...................... | 364/550 |
| 5,224,381 | | 7/1993 | Sandoz et al. ......................... | 73/597 |
| 5,357,112 | * | 10/1994 | Steele et al. ......................... | 250/340 |
| 5,394,097 | * | 2/1995 | Bechtel et al. ...................... | 324/687 |
| 5,585,732 | * | 12/1996 | Steele et al. ......................... | 324/663 |
| 5,654,643 | * | 8/1997 | Bechtel et al. ...................... | 324/687 |
| 5,873,182 | * | 2/1999 | Fuller .................................... | 34/527 |
| 5,960,104 | * | 9/1999 | Conners et al. .................... | 382/141 |
| 6,026,689 | * | 2/2000 | Snyder et al. ......................... | 73/602 |

OTHER PUBLICATIONS

Kliger et al., "Variability in Wood Properties and its Effect on Distortion and Mechanical Properties of Sawn Timber", Proceedings of the CTIA/IUFRO Int'l Wood Quality Workshop, pp. Vi–15—Vi–22, Aug. 18–22, 1997, Quebec City, Canada.*

Fridley, Kenneth J., et al., Modelling Three–Dimensional Distortion of Wood Due to Anistropic Shrinkage:, Mathl. Comput. Modelling vol. 17, No. 9, pp. 23–30 (1993).*

Beard, et al., "The Influence of Growth Characteristics on Warp in Two Structural Grades of Southern Pine Lumber," *Forest Prod. J.* 43:51–56 (1993).

Brazier, "An Assessment of the Incidence and Significance of Spiral Grain in Young Conifer Trees," *Forest Prod. J.*, 308–312 (1965).

Kliger et al., "Variability in Wood Properties and its Effect on Distortion and Mechanical Properties of Sawn Timber," *Proceedings of the CTIA/IUFRO Int'l Wood Quality Workshop*, pp. Vi–15–Vi–22, Aug. 18–22, 1997, Quebec City, Canada.

Wagner et al., "Impact of Log Sweep on Warp in Southern Pine Structural Lumber," *Forest Prod. J.* 45:59–61 (1995). (Incomplete).

Pamphlet for Model 520 Grain Angle Indicator, Metriguard, Inc., more than one year prior to the filing date of the present application.

Pamphlet for Sylvatest®.

Sandoz et al., "Sylvatest Automation in Sawmill."

Sandoz et al., "Log Grading by Ultrasound (BOIPAC Project)."

Sandoz et al., "Industrial Realisation of Sylvatest for Timber Grading (completed)."

Sandoz et al., "Decay Detection on Living Trees and Grading (FORUS: Ultrasound Testing in Forests)."

Sandoz et al., "Analysis of the Acousto–Ultrasonic Signal for Non–Destructive Evaluation of Wood Properties."

Sandoz, "Ultrasonic Solid Wood Valuation in Industrial Applications," $10^{th}$ Int'l Symp. Nondestructive Testing of Wood, Sep. 26–28, 1996, Lausanne CH.

A.N. Faulger's, "Through–Bark Measurement of Grain Direction; Preliminary Results," *Forest Sci.* 15:92–94 (1969).

Ormasson et al., Influence of Annual Ring Orientation on Shape Stability of Sawn Timber, $5^{th}$ International IUFRO Wood Drying Conference, pp. 427–436 (1996).

Galligan et al., Piezoelectric Effect in Wood, Forest Products Journal, pp. 517–524 (1963).

* cited by examiner

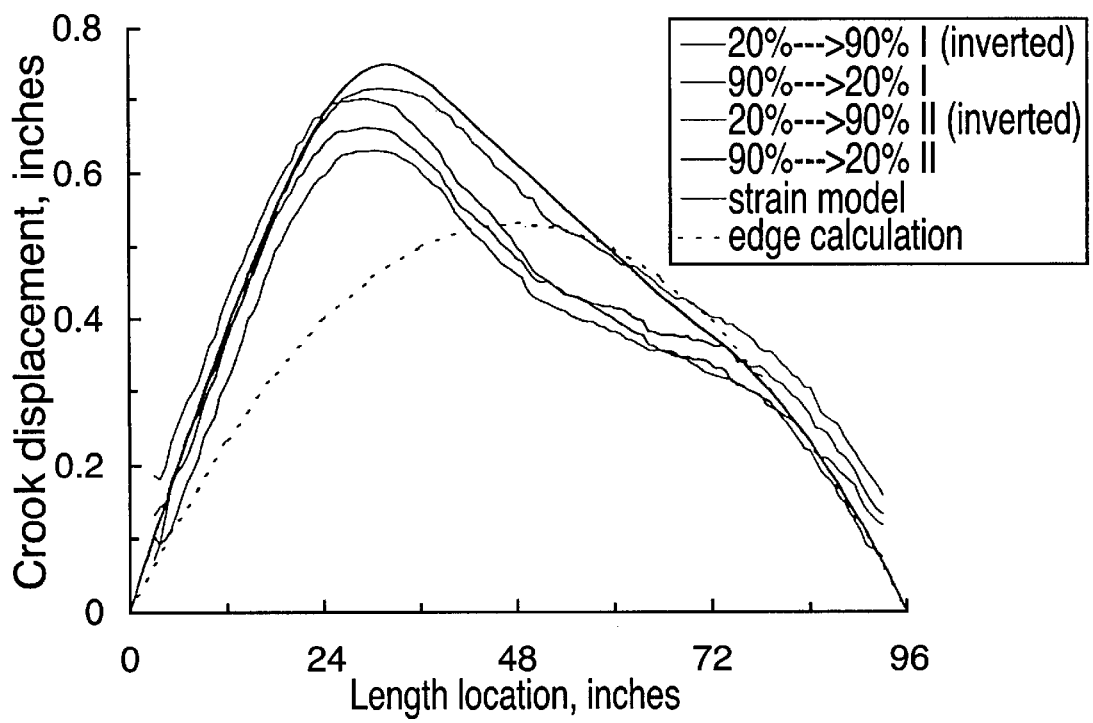
FIG. 8  Board 54-16A
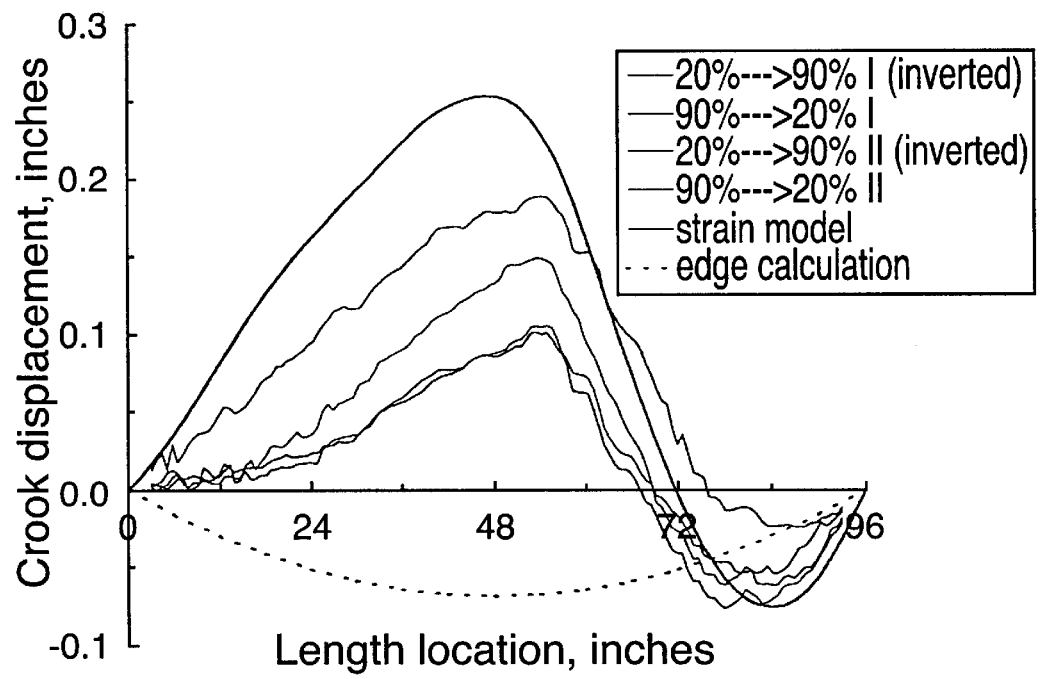
FIG. 9  Board 54-14A

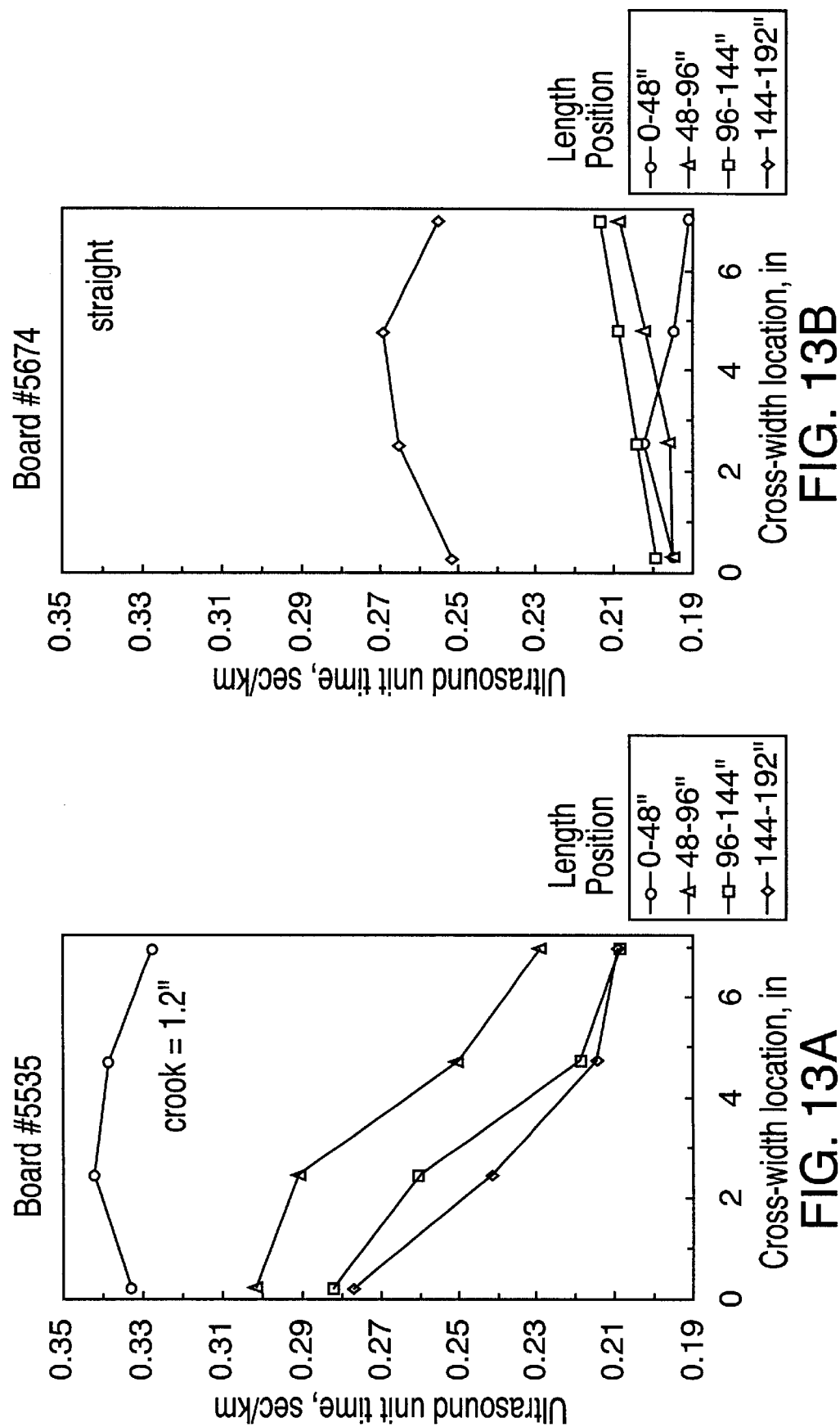

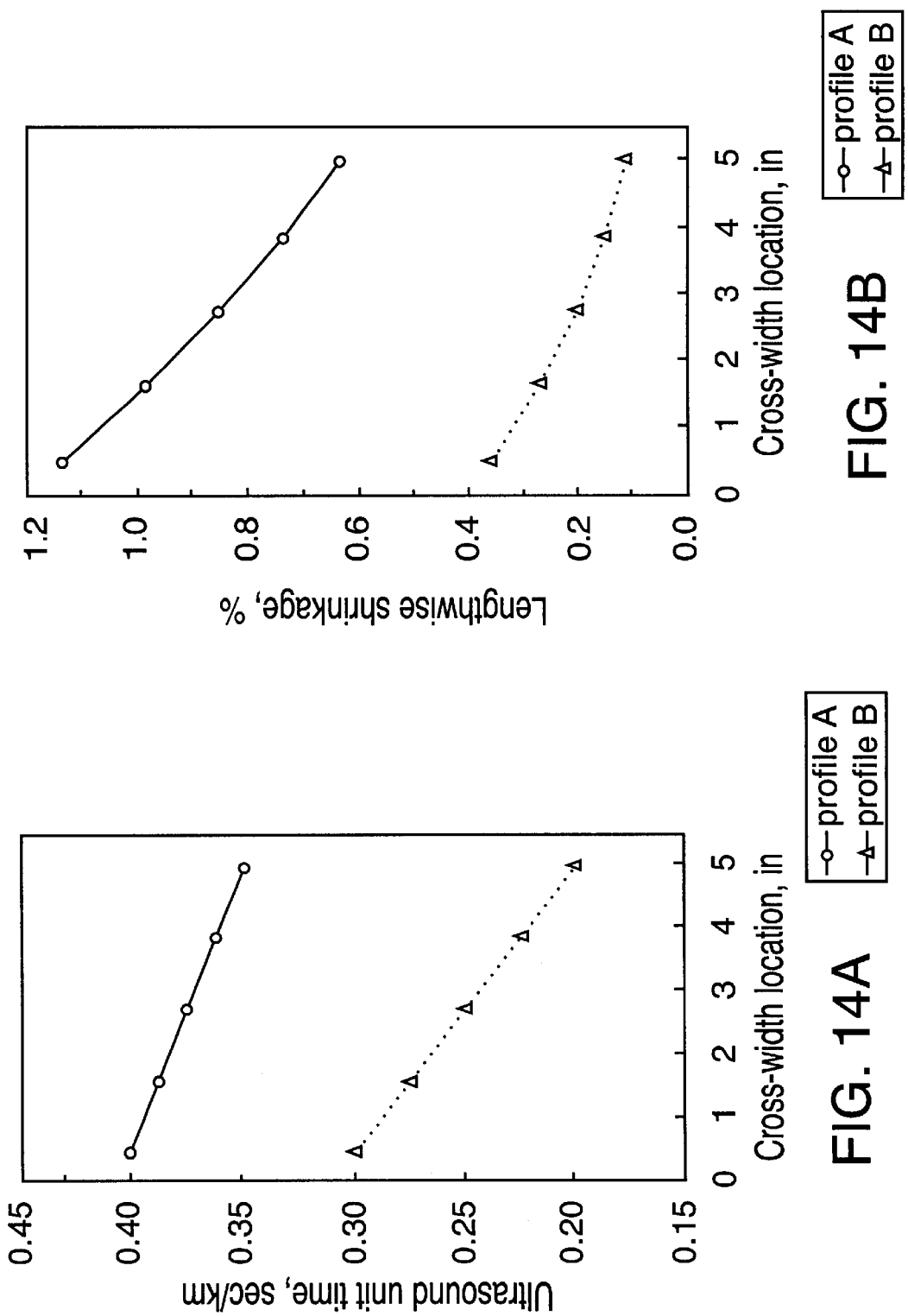

METHOD FOR DETERMINING CROOK POTENTIAL IN WOOD

CROSS REFERENCE TO RELATED APPLICATION

This application claims priority from co-pending U.S. provisional patent application No. 60/098,980, filed on Sep. 2, 1998, which is incorporated herein by reference.

COMPUTER PROGRAM LISTING

A CD-ROM containing a computer program listing appendix has been submitted and is herein incorporated by reference. The CD-ROM contains a single ASCII text file named "DIMENS.txt," created on May 9, 2001, 28 KB in size.

FIELD

The present invention concerns a method for determining crook potential in wood including, without limitation, trees, logs, processed logs, lumber and manufactured wood products.

BACKGROUND

Warp stability of lumber and wood products is an increasingly important consideration. Three types of warp, known as crook, bow, and cup, can be traced to differential length change within a board. FIG. 2 of Perstorper et al., Quality of timber products from Norway spruce, WOOD SCI. TECH. 29 (1995), 339–352, incorporated by reference herein, illustrates different types of warp. Crook refers to in-plane, facewise curvature of wood relative to a longitudinal axis. Bow refers to in-plane facewise curvature relative to a longitudinal axis. Crook and bow are closely related and differ primarily according to the planar surface used to define the warp. Crook refers to in-plane, facewise curvature of wood relative to a length axis. Twist, another type of warp, refers to a rotational instability about an axis of wood (usually the longitudinal axis). Twist appears to be associated with varying grain angle patterns (Brazier). Warp tendency apparently is influenced by a myriad of factors (see Table 1).

TABLE 1

| Factor | Reference Authors |
|---|---|
| Compression wood | Ying, Kretschmann, Bendtsen |
| Drying stresses | Martensson and Svensson |
| Earlywood vs. late wood | Kifetew, Lindberg, Wiklund; Pentoney |
| grain angle | Balodis, Ormarsson |
| log sweep | Taylor and Wagner |
| Longitudinal shrinkage | Ormarsson; Simpson and Gerhardt; Ying, Kretschmann, Bendtsen: McAlister and Clark |
| Microfibril angle | Barber and Meylan; Tang and Smith; Ying, Kretschmann, Bendtsen; Walker |
| Moisture content gradients | Simpson and Gerhardt |
| radial and tangential shrinkages | Kifetew, Lindberg, Wiklund; Meylan |
| Specific gravity | Pentoney; Ying, Kretschmann, Bendtsen |
| stress and strain | Ormarsson; Sandland; Hsu and Tang; Fridley and Tang; Simpson and Gerhardt, Iridayaraj and Haghighi |

Dimensional and warp stability have always been valued attributes. Furthermore, new products emerging from dimension lumber, such as premium-grade joists and studs, require superior dimensional and warp stability performance. The ability to quantify warp potential of wood products would enhance the capability of the forest products industry to service these important markets.

Moreover, inefficient processing of raw timber and lumber wastes tremendous forest resources. Lumber warp reduces product grade and product value. Additionally, warp-prone lumber and lumber products perform poorly in uses or environments unsuitable for warp-prone wood. Millions of dollars are wasted every year because no method exists for efficiently and accurately detecting warp-prone lumber.

If warp-prone wood could be nondestructively identified during or prior to processing and product placement, processing raw timber and lumber into wood products would become more efficient. Raw logs could be culled prior to manufacturing, and wood-products manufacturing processes could be altered to direct raw lumber to various end products according to quality and value. For example, warp-prone trees could be identified while standing in forests or after cutting, and processed into products where warp is an irrelevant consideration (e.g. paper products, chipping, etc.). Green warp-prone lumber could be identified at the mill, separated, and kiln-dried using special warp-reducing techniques (e.g. rapid-drying, high-heat drying, final steaming, restraint-drying, etc.). Lumber having low warp potential could be dried using simpler and more economical methods.

Natural resources are unnecessarily wasted by using certain types of wood in inappropriate applications. If warp tendency of raw logs could be predicted, then warp-prone logs could be processed differently. For example, warp-prone logs could be cut into lumber with cuts being coordinated to reduce warp. The orientation of boards taken from certain logs could be altered to reduce warp, or the thickness of the lumber could be varied, since thicker lumber generally warps less. Alternatively, warp-prone logs could be culled and processed for specific uses (e.g. chipped, lumber for pallets, etc.). Lumber cut from warp-prone logs also could be specially processed (e.g. special kiln drying techniques) or used in selected applications (e.g. relative constant moisture applications).

Additionally, warp-prone lumber could be identified for use in only certain applications. For example, exterior window and door casings experience fluctuating moisture and temperature conditions during use. Warp prone lumber, even if initially straight when dried, could warp in such changing environments. Consequently, if warp-prone lumber could be identified, its use in warp-inducing environments could be avoided. Extremely warp-prone wood may be suitable only for uses where warping is not a significant problem (e.g. for pallets, landscape applications, etc.). In such cases, warp-prone green lumber could be processed without expensive drying techniques.

Warp stability has been studied from both the experimental and theoretical viewpoints. For example, earlier studies explored the links between drying warp and certain lumber characteristics, such as knots, slope-of-grain, and juvenile-wood content [Beard, J., et al., The influence of growth characteristics on warp in two structural grades of southern pine lumber, 43 FOREST PROD. J. 6, 51 (June 1993); Balodis, V., Influence of Grain Angle on Twist in Seasoned Boards, 5 WOOD SCIENCE 44–50 (1972)]. While some relationships were discovered, no commercially viable processes for detecting warp apparently have been developed.

Others have attempted to mathematically model the mechanical phenomena that govern warp instability. A general approach considers elastic, shrinkage, creep, and mechanosorptive elements, including their anisotropic variability and temperature dependence. Such models are complicated. See, e.g., Ormarsson (1995).

Matthews et al.'s U.S. Pat. No. 4,606,645, which is incorporated herein by reference, describes measuring fiber angle in a fibrous solid material relative to three mutually orthogonal reference axes. The '645 patent is understood to teach the measuring and analysis of light reflected from a wood sample to determine the grain angle of the sample. These measurements are then understood to be used in evaluating the strength of the wood. This reference is not understood to relate to determining warp potential of wood.

Kliger et al. teaches a destructive method for analyzing a board. Longitudinal shrinkage was determined by cutting sticks from a piece of lumber, averaging the shrinkage of each stick to determine a single value for longitudinal shrinkage, and modeling crook. Kliger teaches only a fairly approximate method for modeling crook. Kliger's method also depends on destroying the wood piece to determine crook. Furthermore, the authors employed a model which specified only a single radius of curvature whereas warp in wood can occur about more than one radius of curvature.

A practical and accurate method for predicting crook has, despite extensive efforts, not been developed. Additionally, the amount of information which must be known to predict crook has proved daunting.

SUMMARY

A method for determining crook potential of wood is described which addresses the needs and problems identified above. One embodiment of the method comprises nondestructively obtaining lengthwise shrinkage rates of wood, such as standing trees, logs, lumber, or manufactured wood products then determining crook potential of the wood based on the lengthwise shrinkage rates. The method can comprise obtaining lengthwise shrinkage rate information from a third party and then determining crook potential. Alternatively, the method comprises measuring at least one lengthwise shrinkage rate, and typically comprises measuring plural lengthwise shrinkage rates, to determine crook potential.

If the wood comprises lumber, such as a tree having a cant or a board, lengthwise shrinkage rate measurements typically are made on at least one major planar surface of the lumber. The method typically comprises determining lengthwise shrinkage rates at at least two measuring points on the planar surface or on opposed major planar surfaces, separated by a predetermined distance, such as at substantially one-foot intervals.

Particular embodiments of the present invention include determining lengthwise shrinkage rates using infrared radiation, microwave radiation, electricity, acoustic energy, such as ultrasound energy, and combinations thereof. For example, one working embodiment measured the speed of an ultrasound pulse across a certain distance through wood having a certain moisture content. The speed (or velocity) of the ultrasound pulse is used to determine the modulus of elasticity (MOE) of the wood, which can then be correlated to the lengthwise shrinkage rate. In another example, lengthwise shrinkage rate can be determined from the speed of an ultrasound pulse using an empirically derived formula, such as an exponential formula.

Plural lengthwise shrinkage rates also can be determined using this method. Crook potential can then be correlated to actual empirically determined lengthwise shrinkage rates. The method of the present invention can be used to determine crook potential that correlates with actual measured crook with an le value of at least 0.2, typically about 0.5, and preferably 0.6 or greater.

A person of ordinary skill in the art will recognize that the method described herein for determining crook potential can be automated. For example, a computer could be used to determine crook potential, lengthwise shrinkage rates, or both.

Another embodiment of the present invention for nondestructively determining crook potential in wood comprises providing a piece of wood having at least one major planar surface, positioning the piece of wood adjacent to a device for imparting energy through the piece of wood to determine at least one lengthwise shrinkage rate, and determining the crook potential of the piece of wood from the at least one lengthwise shrinkage rate. Infrared radiation, microwave radiation, electricity, acoustic energy, and combinations thereof can be used to determine lengthwise shrinkage rate. Lengthwise shrinkage rates are determined at predetermined intervals along the wood, generally at regularly spaced intervals along the wood, such as substantially one-foot intervals.

The present invention also is directed to an industrial process for commercial production of lumber. For example, an embodiment is directed to determining crook potential of standing trees using the method of the present invention, and then making harvesting and use decisions based on the predictions. Trees could be thinned, for example, based on the crook potential. Another commercial embodiment could be used to determine lengthwise shrinkage rates and crook potentials of raw logs having removed cants (to provide at least one major planar surface), or green lumber, during the milling process.

Still another embodiment of the present invention is directed to a nondestructive method for determining crook potential of wood and comprises obtaining lengthwise shrinkage rates of wood at plural measuring points along the wood and determining crook potential of the wood based on non-averaged lengthwise shrinkage rates. Warp potential is determined using a finite element model (FEM) such as the formula $$\Pi_p = \int \left( \frac{1}{2} \{\varepsilon\}^T [E]\{\varepsilon\} - \{\varepsilon\}^T [E]\{\varepsilon_0\} + \{\varepsilon\}^T \{\sigma_0\} \right) dV - \int_V \{u\}^T \{F\} dV - \int_S \{u\}^T \{\Phi\} dS - \{D\}^T \{P\}$$

In which
- $\{u\} = [u\ v\ w]^T$, the displacement field
- $\{\varepsilon\} = [\varepsilon_x\ \varepsilon_y\ \varepsilon_z\ \gamma_{xy}\ \gamma_{yz}\ \gamma_{zx}]^T$, the strain field
- $[E]$=the material property matrix for an orthotropic material
- $\{\varepsilon_0\}$, $\{\sigma_0\}$=initial strains (including shrinkage induced strains) and initial stresses
- $\{F\} = [F_x\ F_y\ F_z]^T$, body forces
- $\{\Phi\} = [\Phi_x\ \Phi_y\ \Phi_z]^T$, surface tractions
- $\{D\}$=nodal degrees of freedom of the board representation
- $\{P\}$=loads applied to the degrees of freedom from the external environment
- S, V=surface area and volume of the board representation.

Cook, R. et al., CONCEPTS AND APPLICATIONS OF FINITE ELEMENT ANALYSIS, $3^{rd}$ Ed, John Wiley and Sons, New York, 1989.

BRIEF DESCRIPTION OF THE DRAWINGS

FIG. 8 illustrates a comparison of crook potential determined by the present invention and crook predicted by another method.

FIG. 9 illustrates a comparison of crook potential determined by the present invention d crook predicted by another method.

FIG. 13A–13B illustrate ultrasound profiles for crooked and straight wood samples.

FIGS. 14A–14B illustrate a comparison between ultrasound profiles with corresponding lengthwise shrinkage rate profiles.

DETAILED DESCRIPTION

A. Introduction

Empirical studies and a finite element model (FEM) simulation have been conducted to identify causative factors of crook from among a collection of possible warp-related factors (see Table 1). These studies provided a fundamental understanding of warp mechanisms, established the relative importance of causative factors, and allowed the development of a method for predicting crook. This program employed warp measurements of lumber from prior drying studies and physical testing of the same lumber to quantify its mechanical properties.

Crook potential of wood was determined using a pattern of local lengthwise shrinkage rates within the wood. Acoustic velocity in wood, such as ultrasound velocity in wood, was related to the magnitude of the wood's lengthwise shrinkage rates.

Figure 1B:
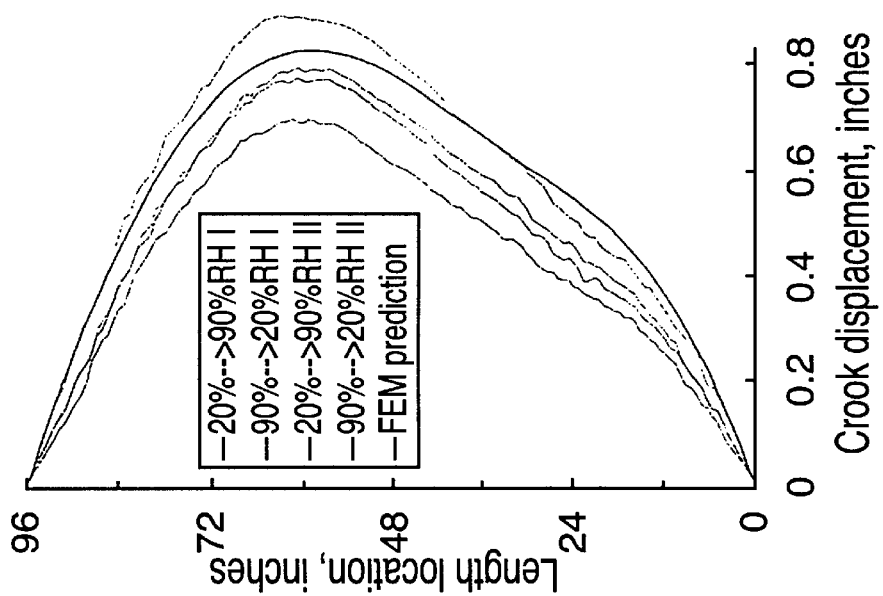
FIG. 1 illustrates determining crook potential from lengthwise shrinkage rates.
Figure 1A:
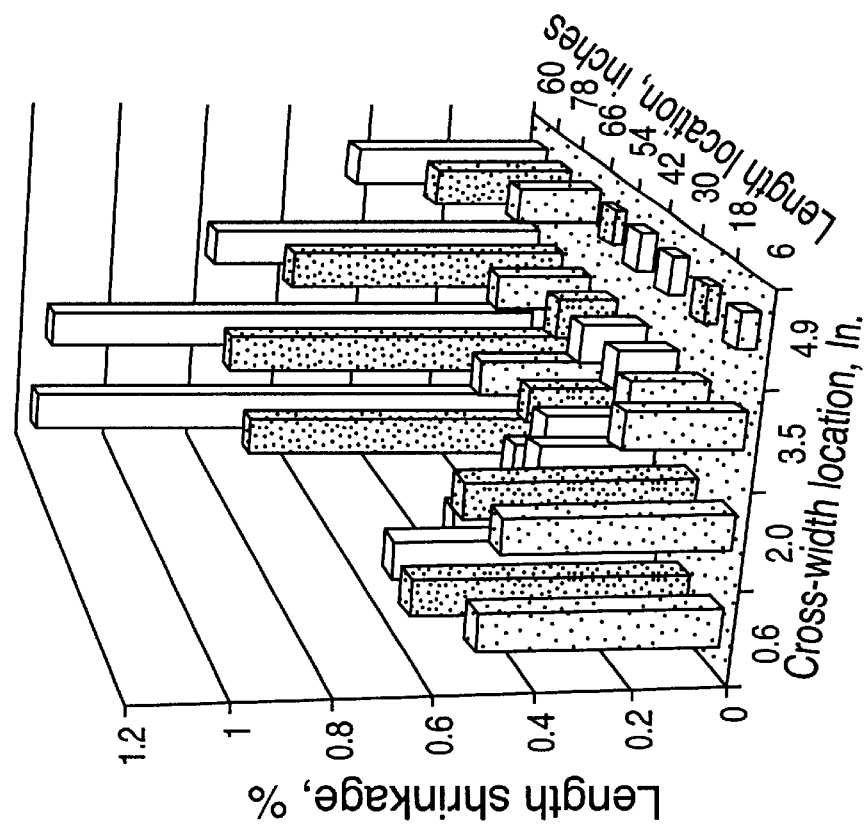

Localized measurement of acoustic velocity in wood, such as ultrasound velocity in lumber, was used to quantify patterns of lengthwise shrinkage rates in sufficient detail to enable practical determinations of crook potential in the wood. As seen in FIG. 1, lengthwise shrinkage rates can be measured at different locations on a board and compiled to form a lengthwise shrinkage map (FIG. 1A). This map can then be used to determine the crook potential of the piece (FIG. 1B). FIG. 1B shows the determined crook potential (labelled "FEM prediction" in the graph legend) and the actual crook measured during different drying cycles. A total of four different cycles were performed: two cycles of drying the wood from an environment of 90% relative humidity (RH) to an environment of 20% RH; and two cycles of changing the relative humidity from 20% RH to 90% RH.

Figure 2:
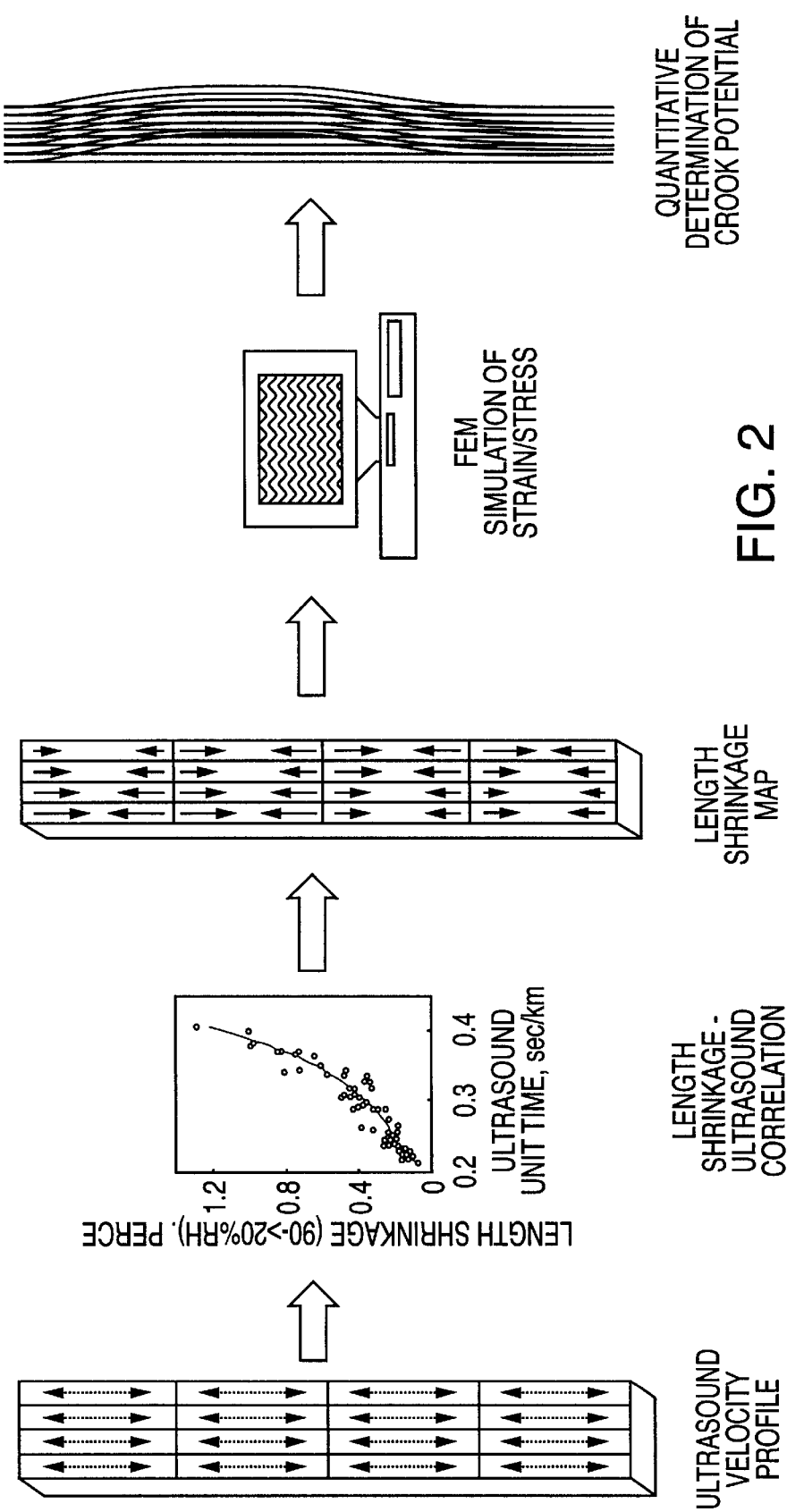
FIG. 2 illustrates one working embodiment of the invention.

FIG. 2 provides an overall picture of one embodiment of the present invention. Lengthwise shrinkage rates can be correlated to ultrasound velocity. Therefore, ultrasound velocity can be measured at locations on a piece of wood, such as a board, and compiled to form an ultrasound velocity profile. Once the ultrasound-lengthwise shrinkage relationship is quantified, the ultrasound velocity profile can be converted into a lengthwise shrinkage map. The data comprising the lengthwise shrinkage map can then be entered into a computerized finite element model (FEM) simulation of strain and stress components of the board. One such model described below is the DIMENS model. The FEM simulation then quantitatively determines the crook potential for the piece of wood.

Figure 3:
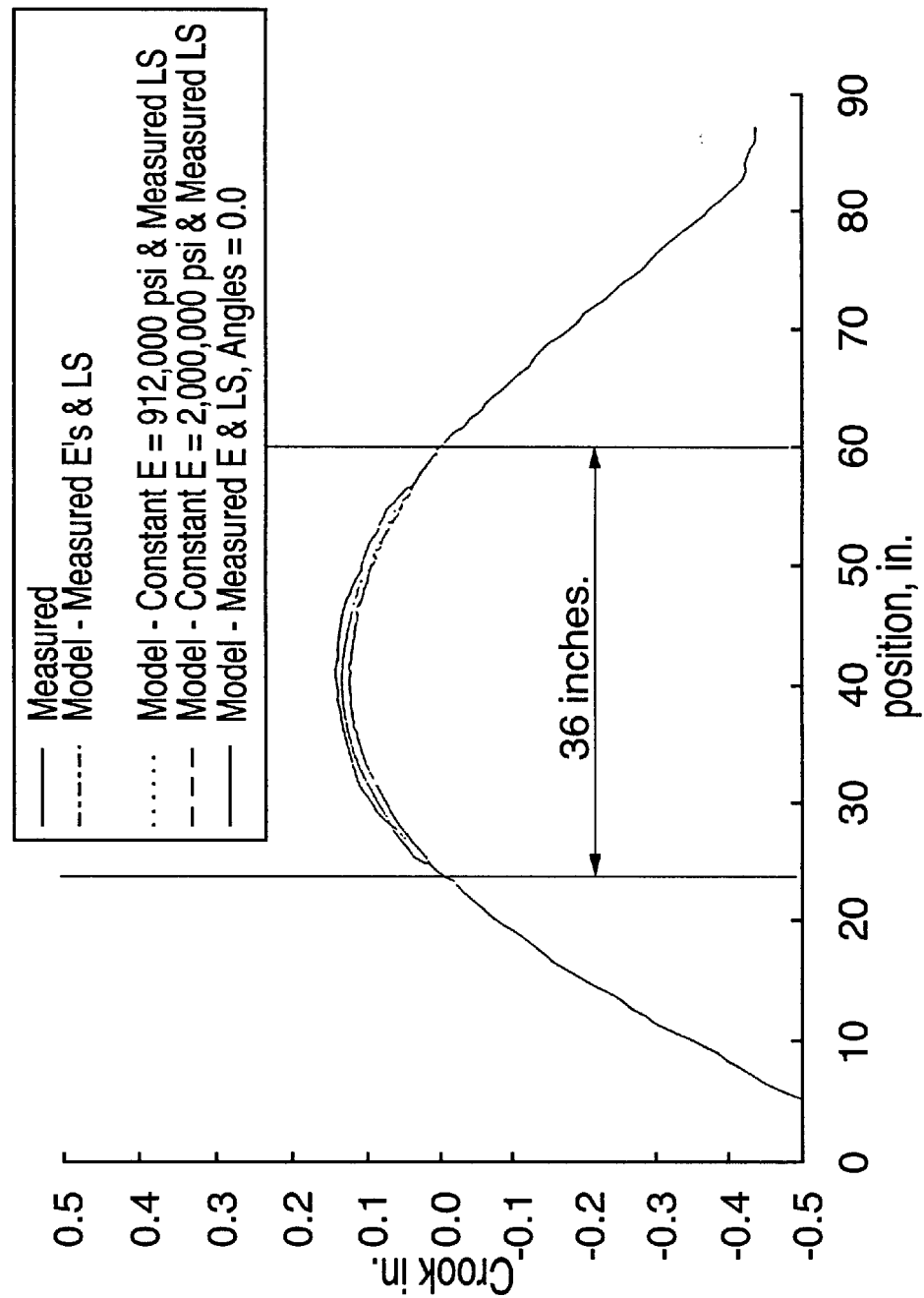
FIG. 3 illustrates the correlation between measured crook versus predicted crook and the effects of MOE and grain angle on the accuracy of determining crook potential.

Once a crook potential is determined, the accuracy of that determination can be assessed by comparing it to the actual crook. FIG. 3 shows that the accuracy of the determined crook potential depends almost entirely on the measured lengthwise shrinkage rates of the wood. FIG. 3 shows the measured crook experienced by a board during a drying cycle. The board was dried from 18 percent moisture content (% MC) to 5% MC by reducing the environmental humidity from 90% RH to 20% RH. A highly crooked 36-inch region in the middle of the board is set off by vertical lines. Crook potentials determined using four different FEM simulations are represented by dashed lines. Lengthwise shrinkage rates were measured in each case, but the models differed according to whether other wood characteristics were actually measured or represented by an empirical constant. Under the first model (labeled "Measured E's & LS"), the localized modulus of elasticity (MOE) measurements were made. Under the second model (labeled "Constant E=912,000 psi & Measured LS"), a constant MOE of 912,000 pounds per square inch (psi) was used. Under the third model (labeled "Constant E=2,000,000 psi & Measured LS"), a constant MOE of 2,000,000 pounds per square inch (psi) was used. Under the fourth model, localized modulus of elasticity (MOE) measurements were made and the grain angle for the entire piece was set to zero. As shown, the characteristics of MOE and grain angle had very little effect on the model's ability to determine crook potential. Therefore, crook potential can be accurately determined using lengthwise shrinkage rate measurements in an FEM simulation.

Figure 4:
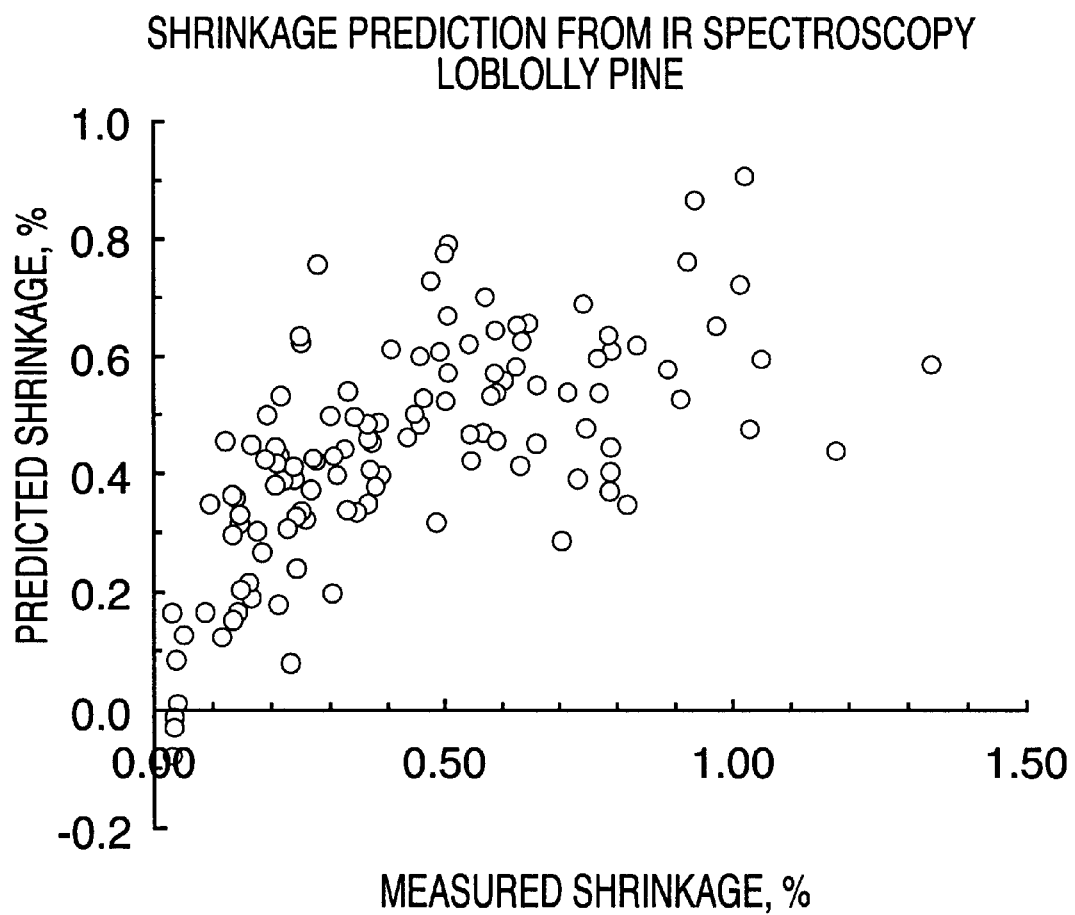
FIG. 4 illustrates the accuracy of infrared radiation to measure lengthwise shrinkage rate.

Transmitting energy (such as acoustic energy) through wood is not the only way to measure lengthwise shrinkage rates. Energy reflected from wood, such as infrared radiation reflected off a planar surface of wood, also can be correlated to the magnitude of the wood's lengthwise shrinkage rates. As seen in FIG. 4, localized infrared (IR) spectroscopic analysis of infrared radiation reflected from lumber can be used to quantify patterns of lengthwise shrinkage rates in sufficient detail to enable practical determinations of crook potential in the wood. FIG. 4 shows the relationship between shrinkage rates predicted based on IR measurements and actual measured shrinkage that occurred during drying. IR measurements were made using a near-IR spectrometer, the Field-Spec spectrometer, obtained from Analytical Spectral Devices, Inc. of Boulder, Colo. Actual shrinkage was measured by exposing specimens to 90% RH, drying to 20% RH, and then measuring actual shrinkage to the nearest $\frac{1}{10,000}$ inch. FIG. 4 demonstrates that measuring lengthwise shrinkage rates using IR spectroscopy is just as accurate as using ultrasound. Therefore, one ordinarily skilled in the art will understand that lengthwise shrinkage can be accurately measured using a variety of techniques as described in more detail below, such as energy transmitted through wood or energy reflected from the surface of wood. The measurement method, or methods, chosen will depend on cost, equipment availability, expertise, harvesting or manufacturing methods, or other considerations.

These and other aspects of the present invention are described below.

B. Terms and Phrases

The following definitions are provided for certain terms and phrases used in this application. These definitions are provided solely for convenience, and should not be construed to provide a meaning having a scope less than would be understood by a person of ordinary skill in the art.

A lengthwise shrinkage rate is the shrinkage rate a particular segment of wood undergoes during drying. There is an important distinction between longitudinal and lengthwise shrinkage rates. Longitudinal shrinkage rate is defined to be shrinkage along the axis of the wood fibers. Lengthwise shrinkage rate parallels the length axis of the piece, an axis of measurement that may or may not be precisely parallel to the fiber direction. Unless the grain angle is zero degrees with respect to a lengthwise shrinkage rate measurement, lengthwise shrinkage rates are differentiated from longitudinal shrinkage rates. For small grain angles, the difference between lengthwise and longitudinal shrinkage rates will be small. As discussed later, if the grain angle exceeds 10 degrees, this difference can become significant and may explain some scatter witnessed in lengthwise shrinkage rate data.

Lengthwise shrinkage rate patterns also closely correlate with modulus of elasticity (MOE) patterns. Modulus of elasticity is a solid property defined to be the ratio of stress-to-strain below the material's elastic limit obtained from a uniaxial test or a bending test. Local MOE variations can be used to predict lengthwise shrinkage rate variations.

Determining warp potential depends on analyzing lengthwise shrinkage rate and grain angle patterns. Such patterns can be determined by measuring absolute shrinkage rates and grain angles or from relative shrinkage patterns and relative grain angle patterns. Determining warp potential of wood does not require measurement of absolute shrinkage rates, so long as the relative shrinkage pattern can be assessed For example, a piece of lumber could have an absolute lengthwise shrinkage rate at a first edge of 1.1% and a lengthwise shrinkage rate at a second edge of 1.2%. The relative shrinkage pattern would be 0.1%. All other pieces having the identical relative shrinkage pattern would have the same magnitude of distortion, such as another piece having an absolute lengthwise shrinkage rate at a first edge of 2.4% and a lengthwise shrinkage rate at a second edge of 2.5%.

A person of ordinary skill in the art will readily appreciate that the method of the present invention is useful for, but is not limited to, analyzing warp potential in lumber. "Lumber" includes wood products processed from raw logs or timber, including planks and boards. Lumber also includes, again without limitation, oriented strand board, fiberboard, paperboard products, straw-based products, etc. Alternative embodiments of the present method can be used to evaluate warp potential of standing timber (i.e. growing trees prior to harvest), raw logs (i.e. harvested trees), and processed logs (i.e. logs made ready for milling).

An embodiment of the present invention can be used to determine crook potential of cut logs. Lengthwise shrinkage patterns of cut logs can be determined by analyzing lengthwise shrinkage as measured at the ends of cut logs. Such measurements can be made in the filed using, for example, spectroscopy. Embodiments of the present invention use methods of light spectrometry to infer shrinkage patterns within the log's cross section by observing the ends of logs. Alternative embodiments infer shrinkage patterns at any wood cross section by extracting and analyzing core samples of wood at that cross section.

An embodiment of the present invention can be used to determine crook potential of wood having at least one planar surface, such as a log having a planar surface (i.e., a cant). Other alternative embodiments can determine warp potential of wood having plural major planar surfaces, such as a board or a plank. Still other alternative embodiments can determine warp potential of standing trees, such as a tree having small portions of interior wood exposed to provide planar surfaces for measuring lengthwise shrinkage rates.

Lengthwise shrinkage rates can be measured at particular "measuring locations" along the wood. A measuring location is understood to be a location on or within the wood where a lengthwise shrinkage rate is measured. For example, working embodiments of the invention measured lengthwise shrinkage rates using ultrasound velocity. Ultrasound velocity can be measured by sending an ultrasound pulse through wood from a first transducer to a second transducer. In such an embodiment, the measuring location would be the segment of wood located substantially around and between the transducers comprising the path of the ultrasound pulse. A measuring location also can refer to a point or small region on a piece, such as if an IR spectroscope probe is used.

Measuring locations may be separated by a predetermined distance. Working embodiments employed measuring locations spaced along one or both edges of a board by a predetermined distance of from about 12 to about 96 inches, more typically from about 12 to about 48 inches. Still other alternative embodiments use a predetermined distance of about a foot for separating measuring locations along the lengthwise span of the board.

Separation distance can be determined for a particular application by considering factors such as the spatial dimensions of the wood being studied, type of wood (e.g. hemlock, Loblolly pine, etc.), and methods used to measure lengthwise shrinkage rates. Not every measuring location needs to be separated by the same predetermined distance, and predetermined distances may vary along the axes of the wood. For example, as seen in FIG. 1, measuring locations were spaced every foot along the length of the wood while spaced approximately every 1.5 inches across the width of the wood. Moreover, one pair of measuring locations might be separated along the edge of a board by a first distance that is the same, substantially the same as, greater than, or less than a second separation distance between a second pair of measuring locations.

As a general rule of thumb, working embodiments have established measuring locations along a width axis by dividing the width by an integer of from about 3 to about 6, typically about 5, and the length axis by an integer of from about 10 to about 15, typically about 12.

FIG. 1A shows lengthwise shrinkage rates taken at 32 such measuring locations specified by eight length locations and four cross-width locations on an eight-foot long, 1 inch by 6 inch board from Loblolly pine (i.e., *pinus taeda*).

Working embodiments of the invention provide "nondestructive" methods for determining crook potential in lumber. For example, ultrasound propagation measurements were used to determine crook potential in a piece of wood (see, e.g., FIG. 2). As another example, IR spectroscopy can be used to measure lengthwise shrinkage rates (see FIG. 4), and these lengthwise shrinkage rates can be used to determine crook potential in a piece of wood.

"Nondestructive" means that the wood used in practicing the present invention is not significantly harmed or damaged and the piece is not significantly materially altered by the method of the present invention. For example, in working embodiments of the present invention, lengthwise shrinkage rates were established using energy transmission speeds or velocities, such as ultrasound velocity. No material was removed from the piece of wood studied and the wood was not damaged by practicing the method. By comparison, prior methods determined lengthwise shrinkage rates by removing large segments of wood (sometimes referred to as "sticks") from the piece, or by cutting the wood entirely into smaller pieces, both of which methods significantly materially altered the piece of wood being studied. Such significant material alteration caused the wood to be destroyed entirely, or, at the very least, rendered useless for structural applications (see, e.g., Kliger et al.).

C. DIMENS Model

A three-dimensional FEM for lumber, called DIMENS, was developed which successfully and accurately determines crook potential given lengthwise shrinkage rates. Additional information concerning the development of the DIMENS model is provided below in Example 2. Appendix A provides source code for one embodiment of a suitable DIMENS model.

The DIMENS model describes the strains that arise in a piece of lumber as a result of the shrinkage that accompanies a change in moisture content. In the DIMENS model, local strains were initially determined by a number of localized physical parameters, including moisture-related shrinkage coefficients, normal and shear moduli of elasticity, and fiber grain angles. It was later determined that crook is primarily related to the variation of lengthwise shrinkage rates (see FIG. 3). In contrast, the magnitude and variation of other factors, including grain angle and MOE, have little effect on determining crook potential (see FIG. 3).

For example, crook potentials were determined using the DIMENS model and particular constant MOE values selected from the range of from about 200,000 psi to about 5,000,000 psi, more typically from about 500,000 psi to about 2,000,000 psi, yet the variance of these crook potentials was insignificant (see FIG. 3). The influence of grain angles apparently was captured in measurements of lengthwise shrinkage rates, and hence crook potential can be accurately determined by analyzing lengthwise shrinkage rates alone and assuming grain angles are already incorporated into the lengthwise shrinkage rate measurements.

The DIMENS model provides a tool for studying the influence of factors affecting dimensional stability of wood and to determine crook potential. Once crook potential is determined, crook can be predicted for a piece of wood undergoing a particular drying regime. Variations in lengthwise shrinkage rates across a piece of lumber were found to be the most important measurement in determining crook potential.

Surprisingly and unexpectedly, measured local grain angle variations were found to have only minor importance in determining crook potential (see FIG. 3, model labeled "Angles=0.0). In other words, grain angle had an insignificant correlation to crook prediction, and incorporating grain angle into the DIMENS model had a negligible effect on determining crook potential. This finding is believed to support the idea that grain angles were captured in measurements of lengthwise shrinkage rates. Therefore, specifically incorporating local grain angle variations in the DIMENS model would, in essence, be accounting for grain angle a second time (in addition to its assumed inclusion in lengthwise shrinkage rate measurements).

Mechanosorptive effects, creep, and other time-dependent complexities of wood behavior could also be ignored in determining crook potential.

Figure 5:
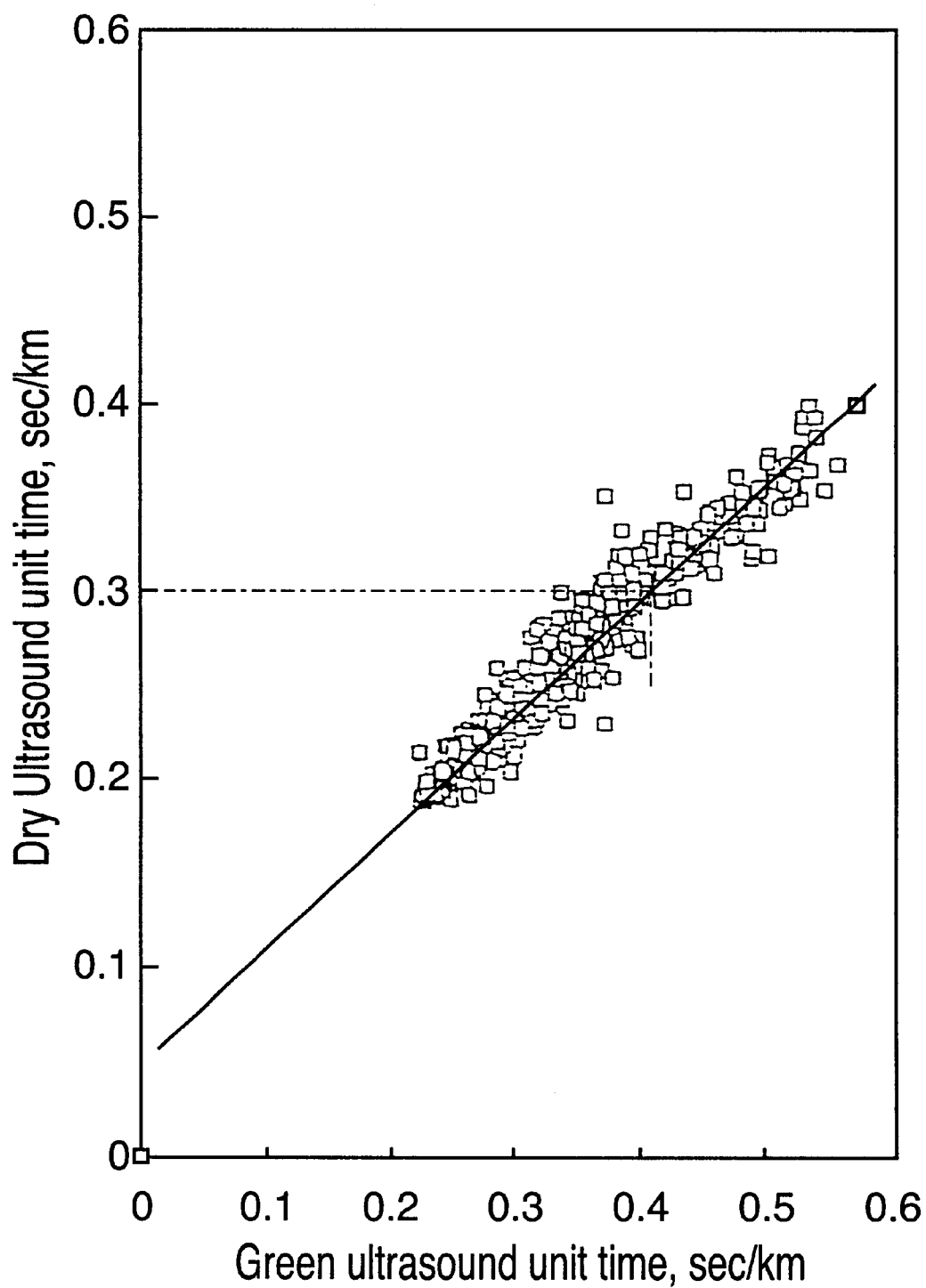
FIG. 5 illustrates a comparison between dry and green ultrasound measurements.

Lengthwise shrinkage rates were found to be closely related to ultrasound velocity in both dry and green samples. FIG. 5 demonstrates that ultrasound unit time ("unit time" the inverse of velocity) in dry wood is closely correlated to ultrasound unit time in green wood, though ultrasound travels faster in dry wood. For example, an ultrasound unit time of 0.30 sec/km in dry wood corresponds to an ultrasound unit time of about 0.40 sec/km in green wood. Ultrasound velocities were measured in 2-foot specimens of green and dry wood by setting the transducers at each end of the specimen and measuring velocity of ultrasound transmission through the specimens.

Figure 6:
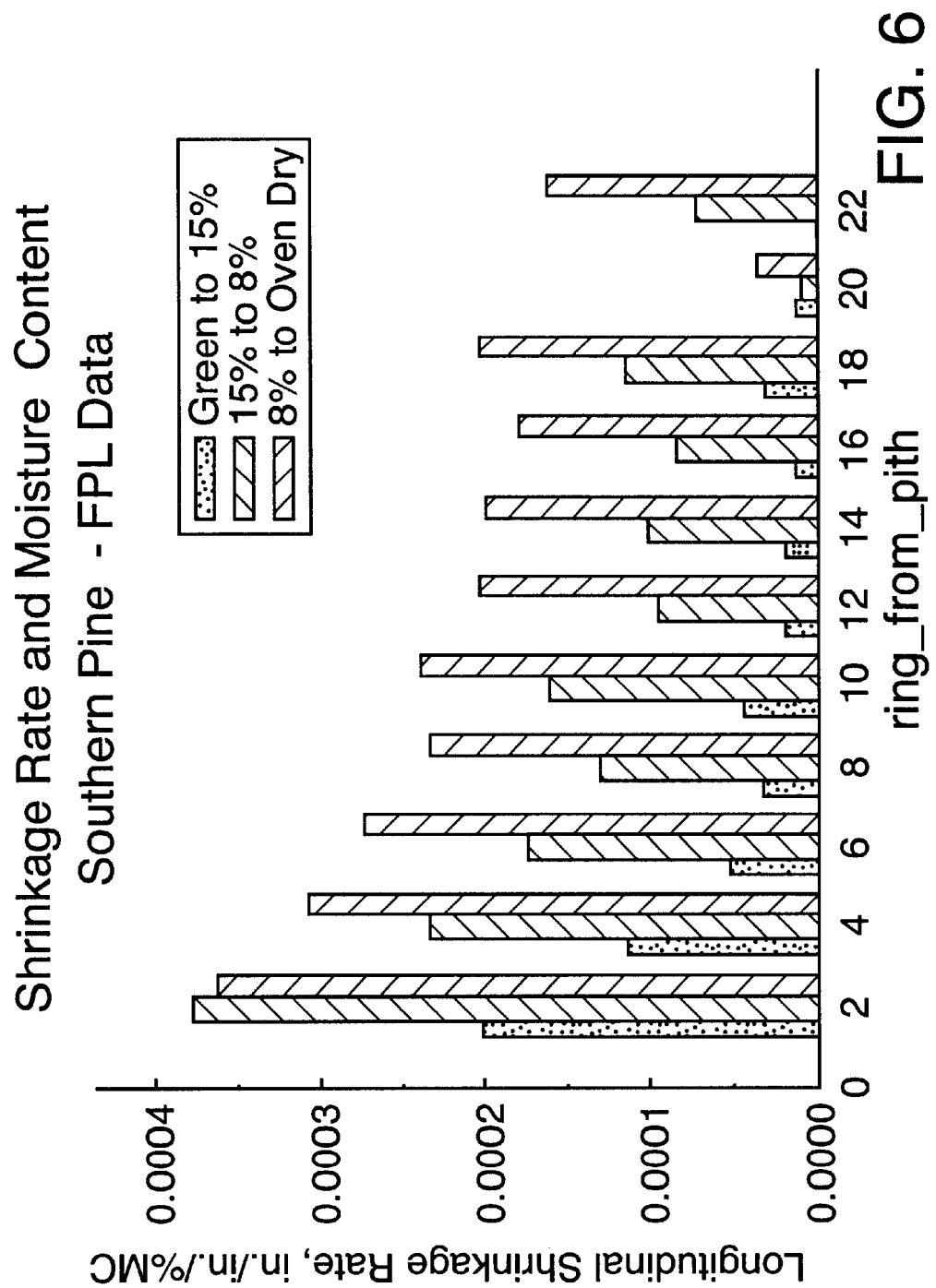
FIG. 6 illustrates a relationship between longitudinal shrinkage rates and distance from pith.
Figure 7:
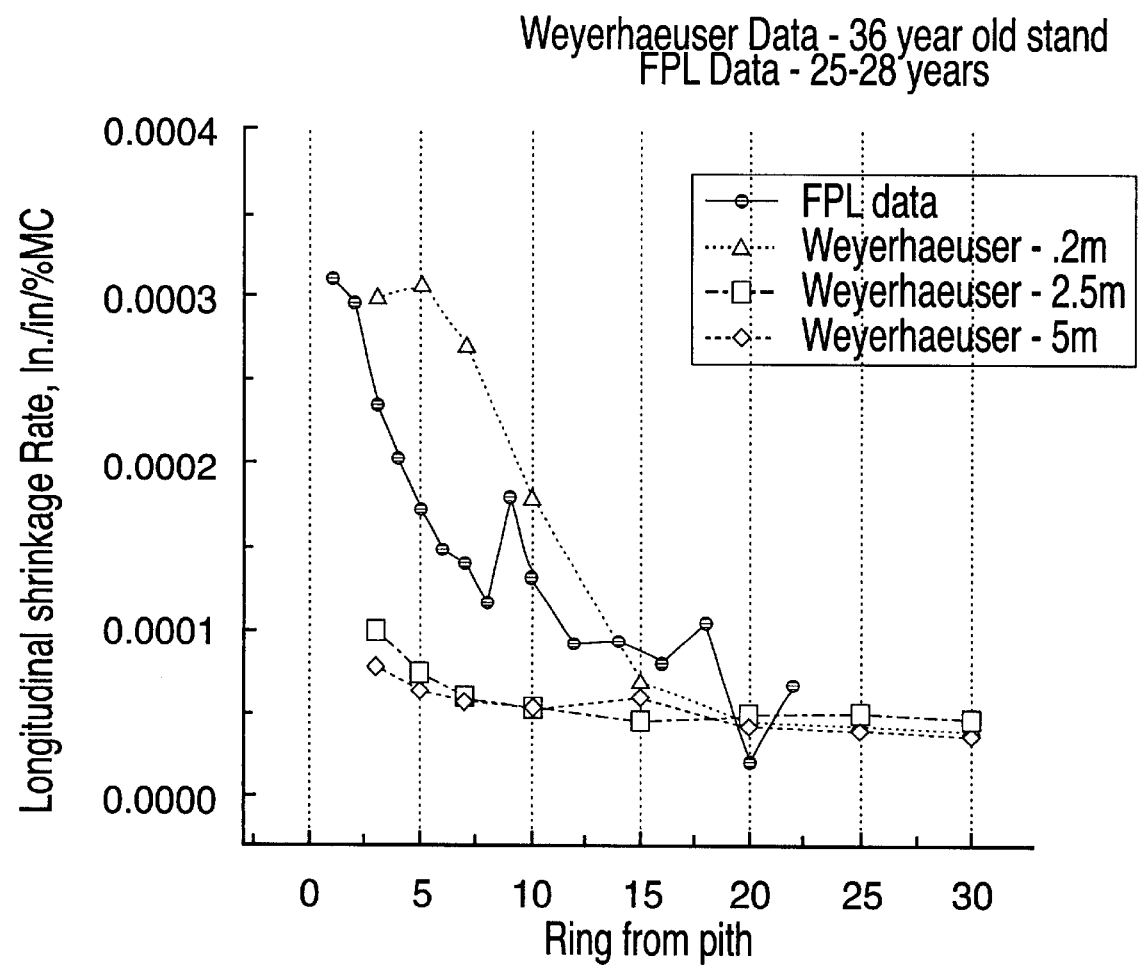
FIG. 7 illustrates measured longitudinal shrinkage rate trends for Loblolly pine based distance from pith.

Distance from pith does not appear to be a reliable predictor of within-board shrinkage rates as demonstrated by FIGS. 6–8. FIG. 6 shows that lengthwise shrinkage rates predicted according to distance from pith (i.e. ring from pith) vary considerably according to how the wood is dried. The results of this study, labeled "FPL Data," were published in Ying, L., et al., Longitudinal Shrinkage in Fast-Grown Loblolly Pine Plantation Wood, Forest Prod. J. 44(1):58–62 (1994). Since predicted lengthwise shrinkage rates varied considerably according to drying regime, lengthwise shrinkage rates cannot be accurately determined by measuring distance from pith.

FIG. 7 shows that lengthwise shrinkage rates predicted according to distance from pith also vary considerably according to the height in the stem of the tree where the distance from pith measurements were taken. Four sets of data were collected. The FPL data set is the same as seen in FIG. 6. Each of the Weyerhaeuser data sets was collected by cutting 3-inch disks from Loblolly pine at the specified heights and removing quarter-inch thick diameter wafers from those disks. As clearly indicated by FIG. 7, lengthwise shrinkage rate predictions based on distance from pith measurements vary considerably according to height in stem. For example, at a distance from pith of 5 rings, predicted longitudinal shrinkage rates varied from about 0.00006 in./in./% MC to about 0.0003 in./in./% MC. Since predicted lengthwise shrinkage rates varied considerably according to the height in stem at which distance from pith measurements were taken, lengthwise shrinkage rates cannot be accurately determined by measuring distance from pith.

Crook potential has been successfully predicted by the DIMENS model based on ultrasound velocity measurements of small samples cut from larger boards. Determinations of crook potential based on ultrasound velocities within uncut boards also were possible. Additionally, ultrasound velocity measurements of both green wood and of dry wood can be used to predict crook tendencies in lumber (see FIG. 5).

Figure 10:
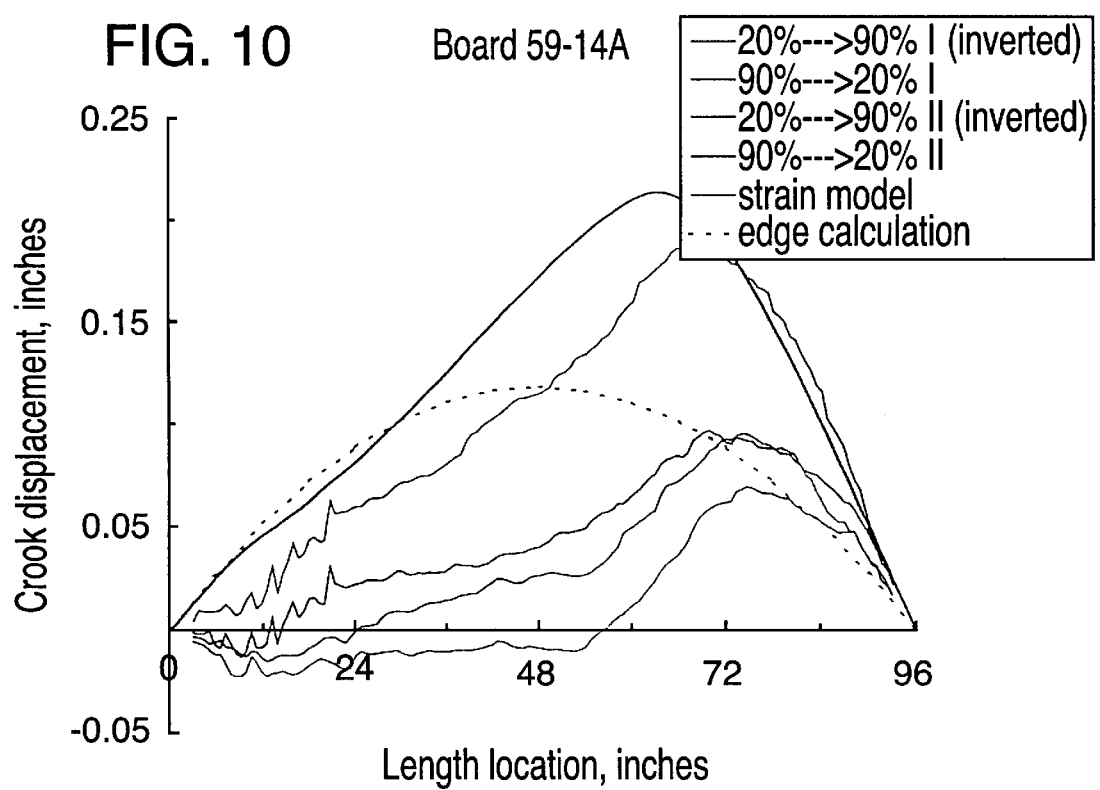
FIG. 10 illustrates a comparison of crook potential determined by the present invention and crook predicted by another method.

Support for the DIMENS model's results is provided in FIGS. 8–10, which compare actual crook behavior with predictions of crook for the same boards based on the crook potential determined by DIMENS. Actual crook was measured by drying and re-moisturizing a particular board. In drying a board, the moisture content of the board was lowered from about 20% db to about 5% db by reducing the relative humidity (RH) of the environment from 90% RH to 20% RH. Boards were re-moisturized by reversing the drying cycle—increasing the relative humidity of the environment from about 20% RH to about 90% RH. The three boards described in FIGS. 8–10 were cut from second-thinning 24 year-old Loblolly pine. Crook potential was determined by DIMENS using specific patterns of lengthwise shrinkage rates. In FIGS. 8–10, the determined crook potential is indicated by a solid line labeled "strain model," actual crook measurements are indicated by thin solid lines, and crook predicted by the prior method of Kliger et al. is plotted using a dashed line (labeled "edge calculation").

The crook potentials shown in FIGS. 8–10 were obtained from measurements of lengthwise shrinkage rates and MOE on three different boards. From each of these boards, a 36-inch long segment that contained the most severe crook was selected. Lengthwise shrinkage rates and MOE were measured on each of nine identically sized 12-inch long specimens sawn from each segment. As shown in FIGS. 8–10, these measured patterns provided calculated results in excellent agreement with the actual crook. In other words, the crook potential determined from measured lengthwise shrinkage rates accurately matched the actual crook of the piece as the piece was dried or re-moisturized.

FIG. 3 shows that accuracy of determining crook potential is not greatly affected if the pattern of MOE is assumed to be uniform throughout the piece of wood, or if the pattern of grain angles is entirely omitted. While a pattern of localized MOE measurements may be used to predict lengthwise shrinkage patterns, practicing the method of the present invention does not require determining an overall MOE for the entire piece of wood.

Figures 11A, 11B:
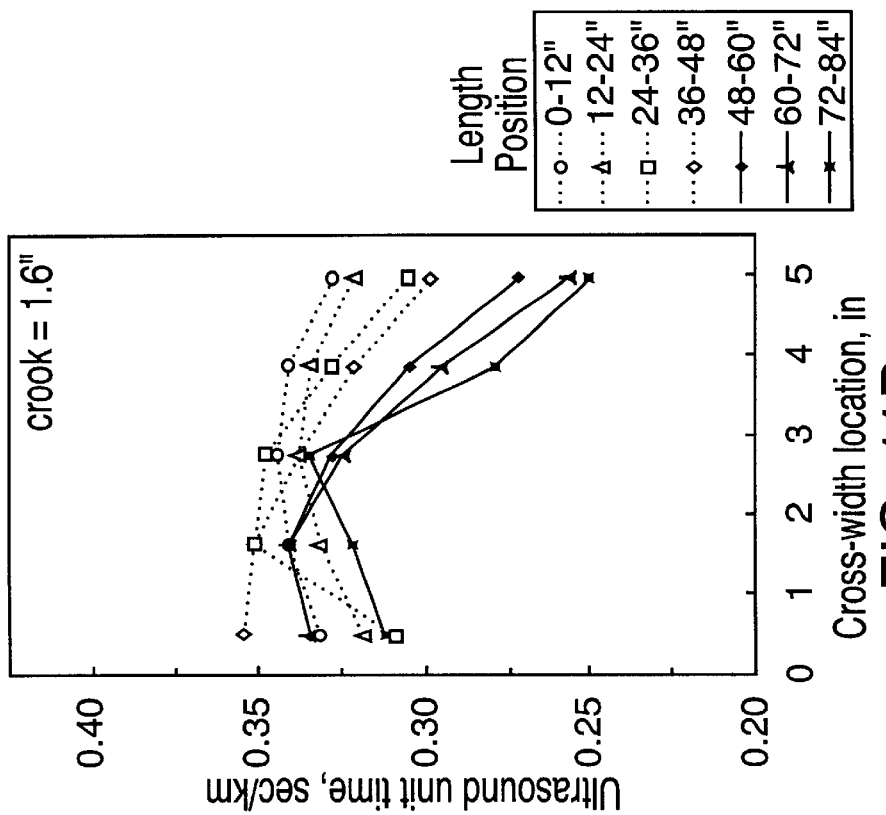
FIGS. 11A–11B illustrate ultrasound profiles for crooked wood samples.

FIGS. 11–13 show that crook-prone lumber exhibits a recognizable gradient, or trend, in lengthwise shrinkage rates across the width of the board. Boards that do not crook exhibit little or no such consistent trend. In each figure, ultrasound unit times—which, as described above, can be correlated to lengthwise shrinkage rates—were measured at regular intervals across the width of the board and down the length of the board. For example, FIG. 11A shows ultrasound measurements taken at one-inch intervals across the width of the board and one-foot intervals down the length of the board. FIG. 13A shows ultrasound measurements taken at two-inch intervals across the width of the board and four-foot intervals down the length of the board.

Figures 12A, 12B:
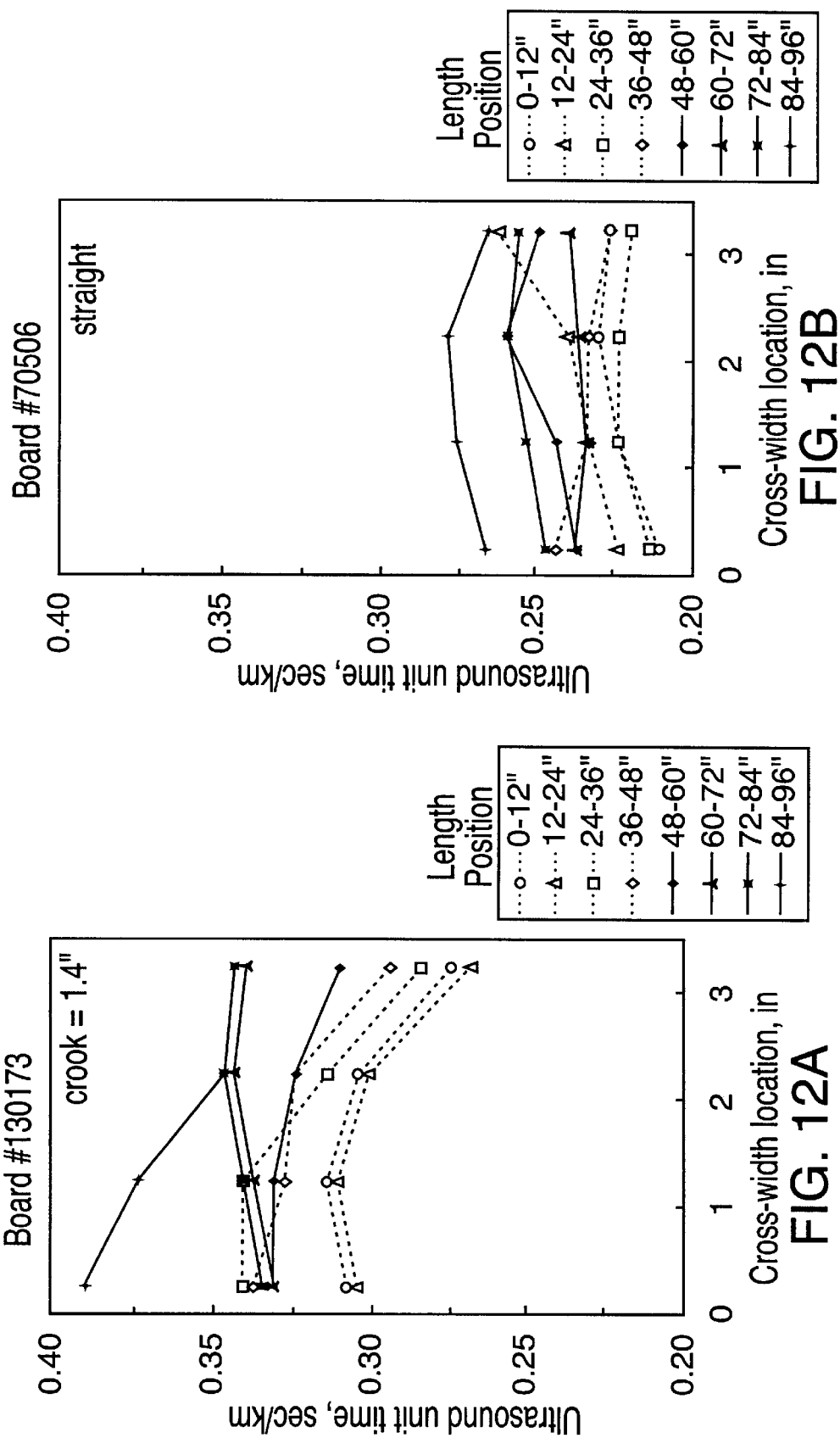
FIGS. 12A–12B illustrate ultrasound profiles for crooked and straight wood samples.

As seen from FIGS. 11–13, crook-prone lumber exhibits a recognizable gradient, or trend, in lengthwise shrinkage rates across the width of the piece while straight lumber exhibits no such recognizable gradient. For example, FIG. 12A shows Board #130173 with a measured crook of 1.4 inches. At length position 84–96 inches, the ultrasound unit time declines from about 0.38 sec/km (at a cross-width location of about 0 inches) to about 0.34 sec/km. With the exception of one length location set of measurements (length position 72–84 inches), all ultrasound measurements at various length positions show a similar declining trend in ultrasound unit time across the width of the board.

In contrast, FIG. 12B shows Board #70506 which exhibited no crook. At each length position, the ultrasound unit time at one edge of the board (cross-width location 0 inches) is substantially the same as the ultrasound unit time at the other edge of the board (cross-width location 3 inches). In other words, the straight board exhibited no recognizable gradient, or trend, in lengthwise shrinkage rates across the width of the piece.

Figure 17:
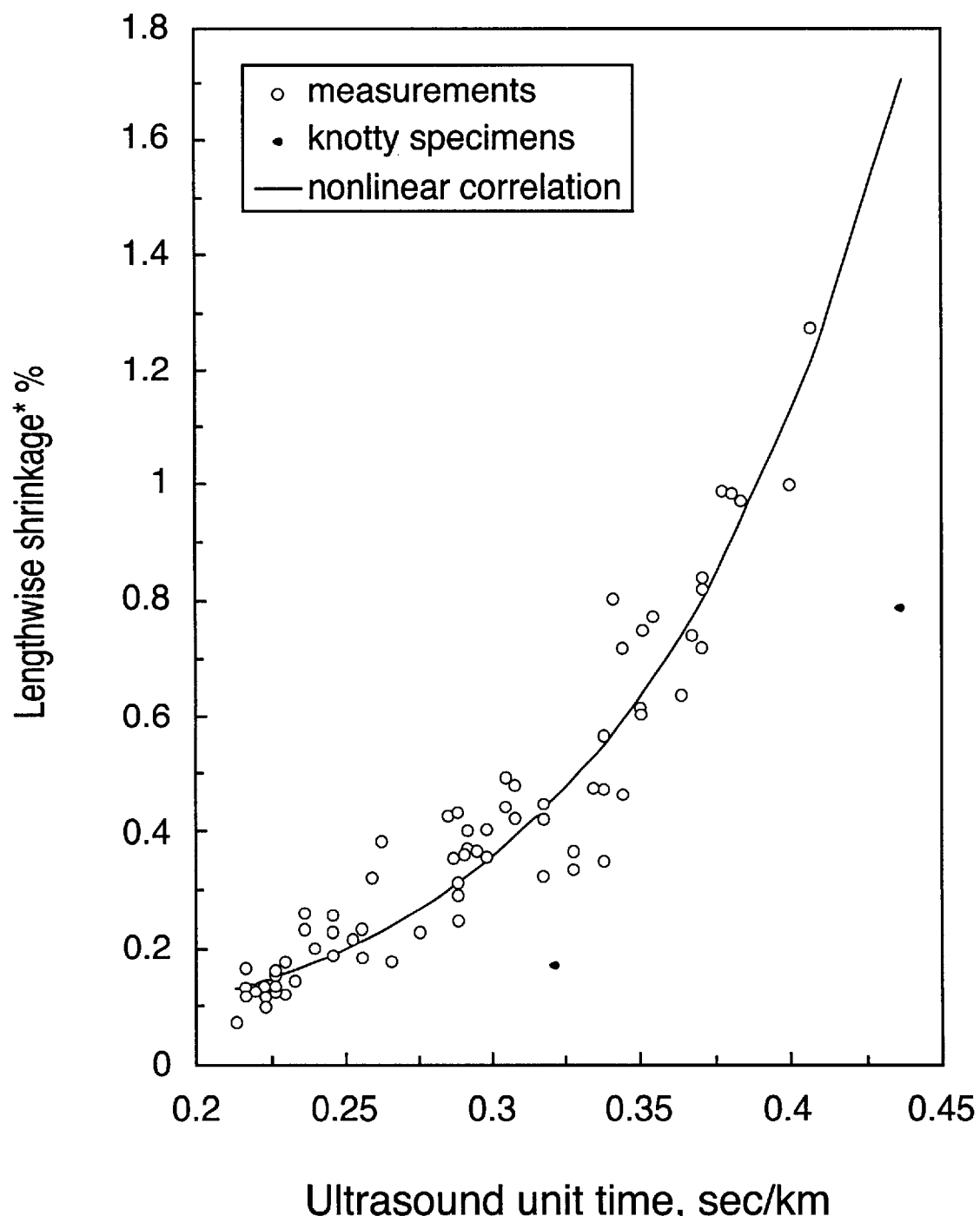
FIG. 17 illustrates the relationship between lengthwise shrinkage rate and ultrasound unit time.

Hypothetical FIG. 14 emphasizes the correlation between ultrasound unit time and lengthwise shrinkage rates, assuming an exponential relationship as seen in FIG. 17. As FIG. 14 shows, a recognizable gradient, or trend, in ultrasound unit time measurements across the width of a piece at one length position would correspond to a similar recognizable gradient, or trend, in lengthwise shrinkage rates across the width of the piece at the same length position. While this relationship would not be linear, it would be consistent and measurable.

Wood with crook potential therefore can be identified by consistently lower lengthwise shrinkage rates within one segment of the piece, and higher lengthwise shrinkage within another segment. However, since it is not possible to directly measure lengthwise shrinkage rates nondestructively, indirect methods have been developed to measure lengthwise shrinkage rates.

Figure 15:
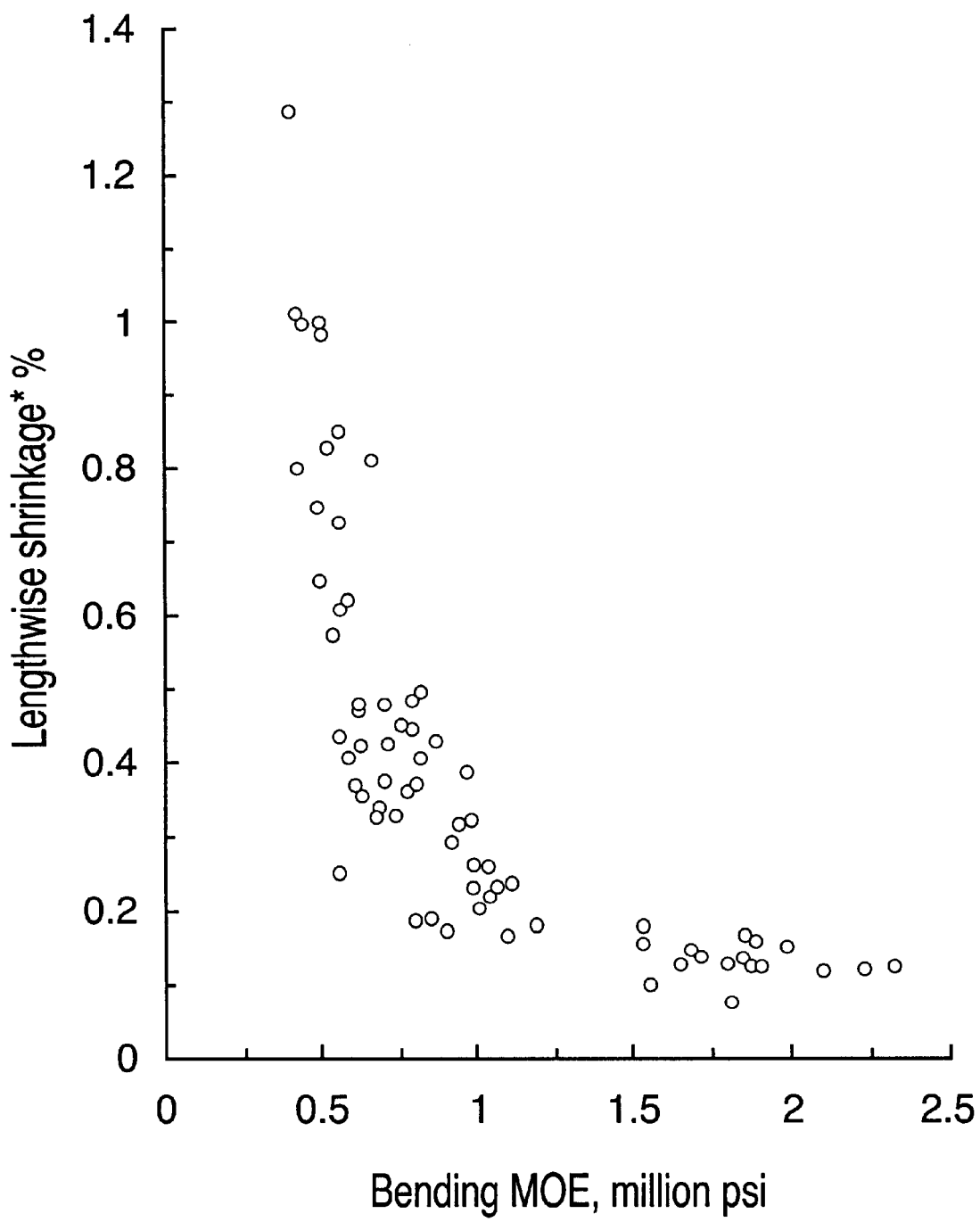
FIG. 15 illustrates the relationship between lengthwise shrinkage rate and MOE.
Figure 16:
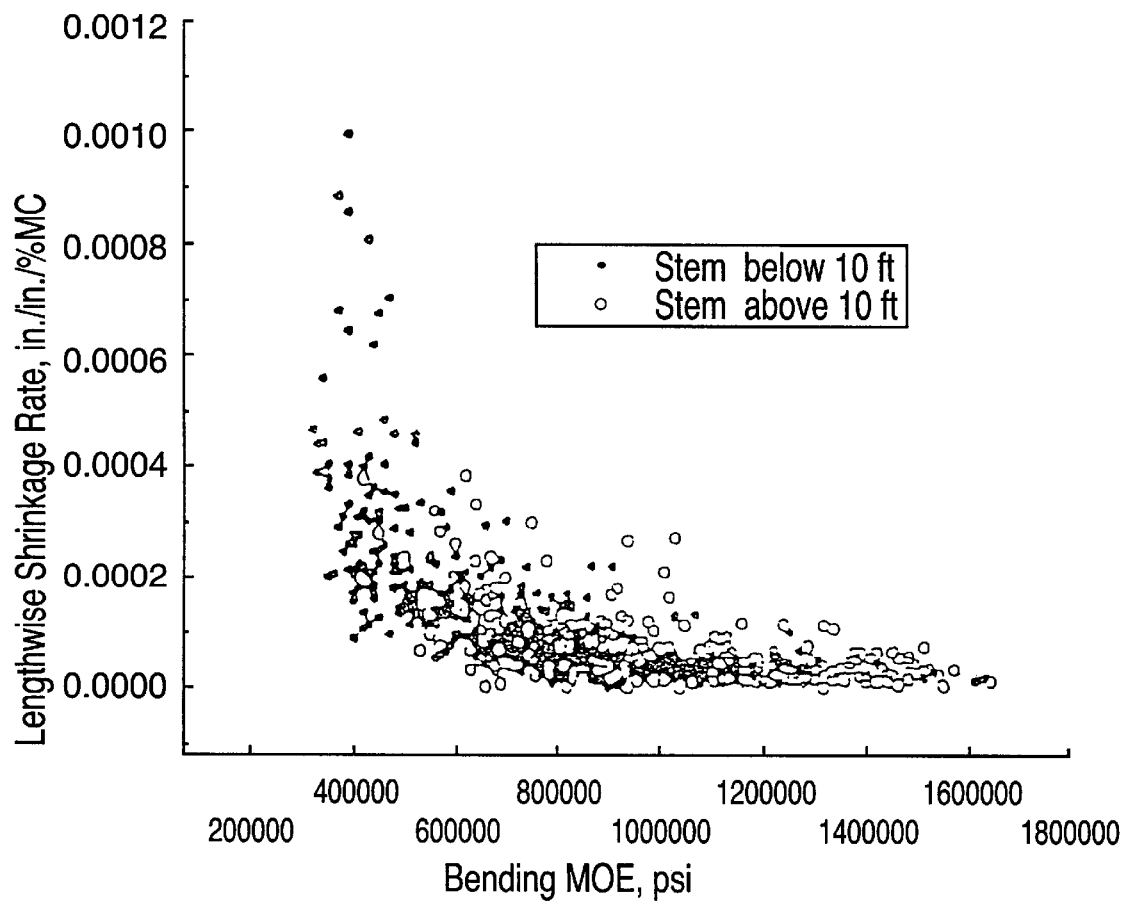
FIG. 16 illustrates mechanical bending MOE as a predictor of lengthwise shrinkage rate.

One such indirect method was developed by measurements on 12-inch long specimens from the 36-inch board segments. This study revealed an inverse relationship between lengthwise shrinkage rate and bending MOE, as shown in FIGS. 15 and 16. Crook potential therefore can be determined from localized MOE measurements.

FIG. 15 shows the correlation between lengthwise shrinkage rates and MOE based on measurements taken on boards from 24 year-old Loblolly pine. The boards were cut into 12-inch sticks and subjected to drying by reducing the environment from 90% RH to 20% RH.

FIG. 16 demonstrates that the correlation between lengthwise shrinkage rates and MOE does not vary according to height in stem (as opposed to the variance seen in predicting lengthwise shrinkage rates based on distance from pith measurements; see FIG. 7). Wood samples were obtained in essentially the same manner as the wood illustrated in FIG. 15.

Determining crook potential by localized MOE measurements is inefficient because making rapid, non-destructive measurements of local bending MOE is difficult. However, MOE can be correlated to ultrasound velocity. Based on the relationship between MOE and lengthwise shrinkage rates, it was determined that lengthwise shrinkage rates could also be correlated to ultrasound velocity. This MOE-lengthwise shrinkage rate relationship is discussed below.

Ultrasound scanning of a number of crooked and straight boards of varied dimensions and from different raw material resources further confirmed that lengthwise shrinkage rates could be correlated to ultrasound velocity. Measurements were made using a commercially available Sylvatest® apparatus, available from Sandes S A, of Granges/Veveyse, Switzerland, which measures the time-of-flight of a 14-kHz ultrasound signal between handheld sender and receiver probes. Other sounding, resonating or velocity testing devices may be utilized, so long as the signal may properly propagate through the wood sample. The probes were positioned on the face of a board at predetermined distances along the board length, and readings of lengthwise unit travel time were taken at measuring locations across the face and along the length of the board.

For raw logs, the probes could be correspondingly located on the surface of the raw log or on the surface of the log from which a cant has been removed. Such measurements also can be taken along the lengths of standing trees. Thus, harvesting decisions could be made in the field. For example, crook prone trees could be harvested early during a thinning operation, which would produce higher-grade lumber, whereas trees having less crook potential could be cut later.

Determining crook potential provides a basis for predicting the actual crook, which will occur during drying, or during cycles of drying and wetting (such as seasonal cycles). Once crook potential is determined, crook can be predicted according to the rapidity, magnitude, and methods of drying. For example, if the piece of wood will be quickly dried over a few days from 30% moisture content (MC) to 15% moisture content (MC), crook can be predicted using the determined crook potential for the piece. Actual crook has been measured after drying and compared to the predicted crook to assess the accuracy of the determined crook potential for the particular piece (see, e.g., FIGS. 8–10).

One of ordinary skill in the art will appreciate that DIMENS provides only one basis for practicing the present invention. Alternative FEM's for determining crook potential could be developed using methods of the present invention.

D. Acoustic Energy

As discussed above, ultrasound velocities can be used to predict crook potential. Ultrasound is one type of acoustic energy, having a frequency range of from about ten kHz to about several megahertz, that can be used to practice the present invention. Acoustic energy also includes frequency ranges other than in the ultrasound range. For example, stress waves, having a frequency range of from about 100 Hz to the ultrasound range, also can be used to practice the present invention. Generally, any acoustic energy having a wavelength less than that of the separation distance between two measuring locations can be used to practice the present invention.

Ultrasound velocities may be measured in a variety of ways. A working embodiment of the present invention employs ultrasound pulses. An ultrasound velocity can be quantified by determining the transmission speed (i.e. the speed at which the pulse is transmitted through the wood) and the direction vector of the ultrasound pulse. Ultrasound velocity can be measured based on one ultrasound pulse or plural ultrasound pulses.

The use of acoustic energy is not limited to such devices, however. A person of ordinary skill in the art will realize that other sounding or resonating devices, or other frequencies may be utilized, so long as the acoustic signal may properly propagate through the wood. For example, the commercially available Sylvatest® apparatus employs acoustic signals in the upper end of the audible range of sound (about 14 kHz). In fact, any device which causes an acoustic signal to propagate through the wood may be used in the present invention, including acoustic signals generated during harvesting, milling, or manufacturing, such as by a saw, planer, or sander.

Based on these results, a working embodiment of the invention employs a measuring device to obtain velocity measurements of acoustic signals in wood. For example, a commercially available Sylvatest® apparatus, which measures the time-of-flight of a 14-kHz ultrasound signal between handheld sender and receiver probes, was used in working embodiments of the present invention. The ultrasound measurements were then used to establish lengthwise shrinkage rates in the wood and thereby determine the crook potential.

For ease of use, all ultrasound measurements discussed herein were performed with the testing device at a single frequency of detection. Multiple frequency testing also could be performed, however.

Because the relationship between lengthwise shrinkage rates and ultrasound unit times is nonlinear, differences in unit times may understate actual differences in lengthwise shrinkage rates. This discrepancy increases with longer unit times as illustrated by the hypothetical example of FIG. 14, which shows how a smaller gradient in unit time (at a higher average unit time) can correspond to a larger gradient in lengthwise shrinkage rate. Since determining crook potential is based on lengthwise shrinkage rates, it may sometimes be important to quantify the shrinkage-ultrasound unit time relationship in order to properly interpret ultrasound measurements and thus accurately determine crook potential.

Infrared (IR) radiation has also been used to measure lengthwise shrinkage rates. Information about wood chemistry can be obtained by IR spectroscopy, and lengthwise shrinkage rates can be estimated from this chemical information. Other methods of analyzing wood chemistry, such as nuclear magnetic resonance (NMR) spectroscopy, could also be used in place of or in addition to IR spectroscopy.

Other embodiments of the invention could determine lengthwise shrinkage rates using any method capable of providing the desired information, particularly microfibril angle, including without limitation, microwave radiation, electricity (to measure dielectric potentials or in analyzing a pizoelectric effect), X-ray diffraction (to measure microfibril angles), and combinations of these methods.

One of ordinary skill in the art will recognize that methods of the present invention can use a single type of energy or different types of energy in combination. Some embodiments employ only one type of energy (e.g. ultrasound only, infrared only, etc.), while other embodiments employ two or more types of energy in combination (e.g. ultrasound and infrared; ultrasound and microwave; infrared and microwave; ultrasound, infrared and microwave; etc.).

Another factor in the practical application of this method is the effect of knots and other wood defects on energy transmissions, such as ultrasound measurements. FIG. 17 demonstrates the effect of knots or other defects. Data for this figure was collected from wood samples obtained in essentially the same manner as the wood illustrated in FIG. 15. In the lengthwise shrinkage rate/ultrasound unit time relationship shown in FIG. 17, the two farthest-outlying data points (shown as solid symbols residing below the general correlation curve) were from specimens containing large knots. This suggests that knots exaggerate unit time, resulting in an overestimation of lengthwise shrinkage rates which can be compensated for to maintain accuracy in determining crook potential.

Knots and other wood defects can be detected by X-ray, such as the CAE-Newnes XLG (x-ray lumber gauge) available from the CAE-Newnes company of Richmond, British Columbia, Canada. or other detection methods. The effects of knots or other defects can, however, be minimized and alleviated.

E. Automation of Method

Determining crook potential may be done by computer, in whole or in part. Working embodiments used one or more computers to measure ultrasound velocities, compute lengthwise shrinkage rates, and determine crook potential. Alternative embodiments employ computers to determine crook potential by processing previously obtained lengthwise shrinkage rates for a piece of wood (e.g. lengthwise shrinkage rate data supplied by a third party). Still other embodiments employ one or more computers solely for FEM modeling to determine crook potential.

F. Green Versus Dry Wood

Figure 18:
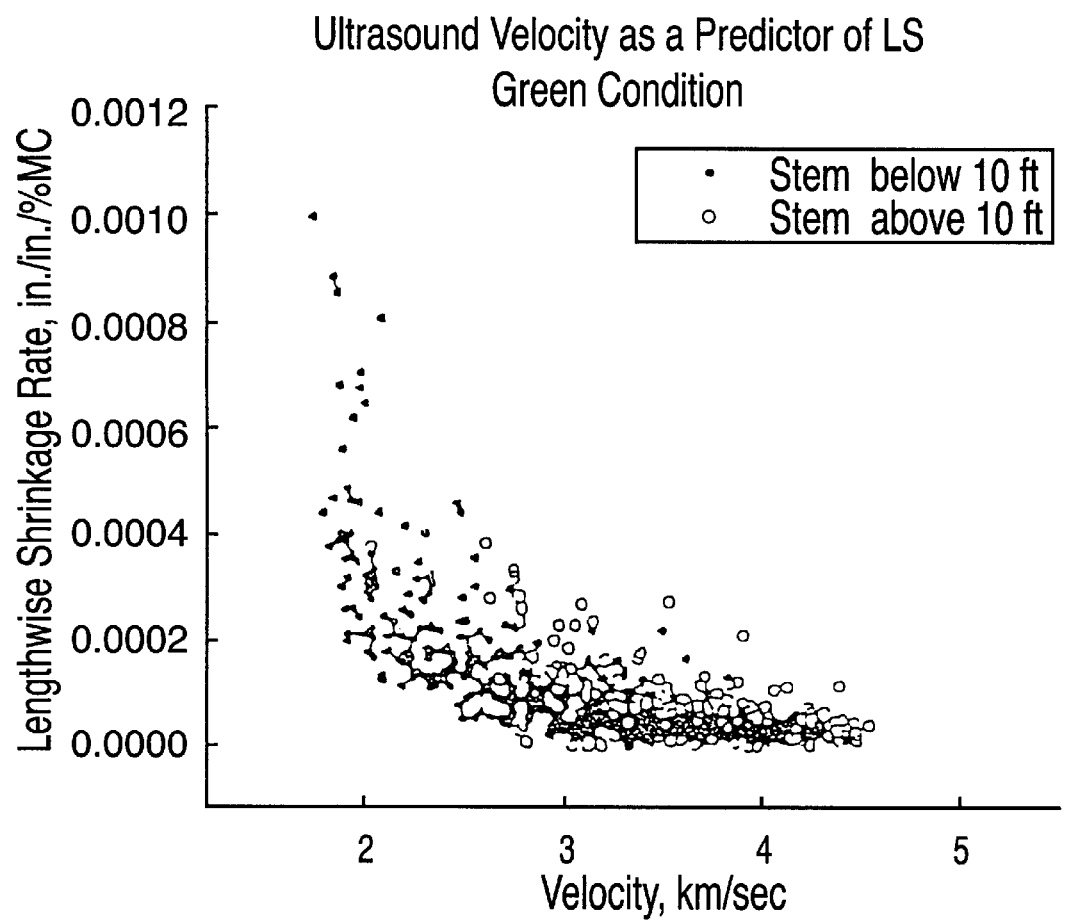
FIG. 18 illustrates ultrasound velocity measured in green specimens as a predictor of lengthwise shrinkage rate.
Figure 19:
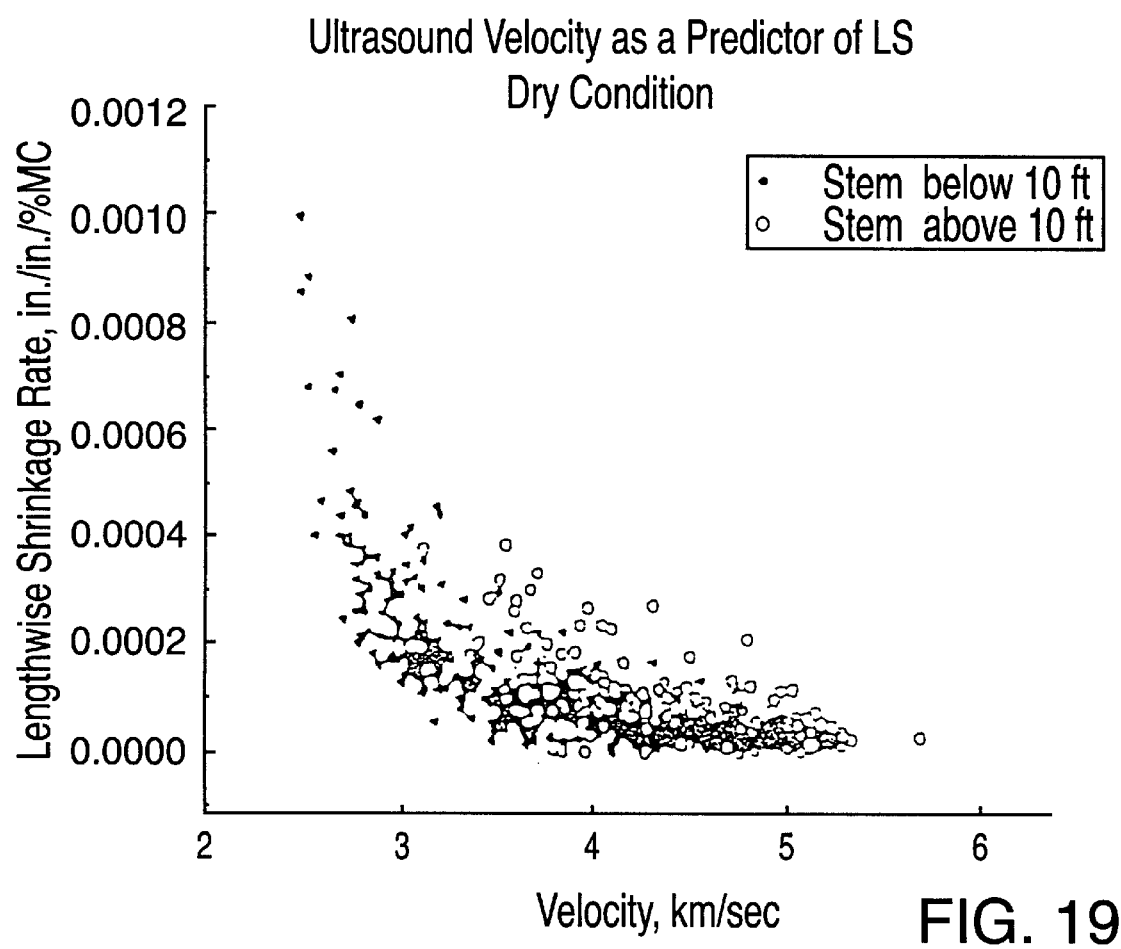
FIG. 19 illustrates ultrasound velocity measured in dry specimens as a predictor of lengthwise shrinkage rate.

A set of ultrasound measurements made on a collection of specimens both before and after drying demonstrates that ultrasound measurements of green and dry lumber are closely related. As shown in FIGS. 18 and 19, the same relationship between lengthwise shrinkage rates and ultrasound velocity measurements are seen in both green lumber and dry lumber. The data displayed in these figures was collected using the same methods as those illustrated in FIG. 16.

Therefore, the methods developed using dry lumber measurements are applicable to green lumber as well.

Furthermore, the method of the present invention can be practiced on wood having any moisture content. Alternative embodiments can be practiced on pieces of wood having moisture contents ranging from fresh cut (over 100% MC) to completely dry (about 0% MC), more typically practiced on pieces of wood having moisture contents ranging from about 0% MC to about 50% MC, even more typically from about 4% MC to about 20% MC.

G. Bow and Cup

As described above, bow exhibits relationships similar to crook. See Perstorper, et al. Therefore, determining bow potential based on lengthwise shrinkage rates also is as feasible as determining crook potential.

Cup potential can be determined using the method of the present invention as well. However, rather than measuring lengthwise shrinkage rates, such embodiments employ measurements of transverse shrinkage rates. In all other aspects, the analysis is the same as that for determining crook potential.

H. EXAMPLES

The following examples are provided to illustrate particular features of the present invention. The scope of the present invention should not be limited to those features exemplified.

Example #1
Ultrasound Measurements of Loblolly Pine

Results are shown in FIGS. 11–12 for 1×6 boards sawn from Mid-South pruned second-thinning Loblolly pine. Using a 12-inch probe separation, ultrasound readings were taken at five locations across the width of the board, at predetermined one-foot intervals along the length of the board. The crooked boards (FIGS. 11A, 11B and 12A) characteristically exhibited relatively high unit times (i.e., greater lengthwise shrinkage rates) at or near one edge of the board, with a trend of unit time decreasing across the width toward the opposite edge. The straight board (FIG. 12B), in contrast, show no consistent trend across the width. FIG. 13 shows results for 16-ft. 2×8's from Mid-South second thinnings. With longer boards, ultrasound unit times were measured using a 48-inch probe separation.

Example #2
Development of DIMENS Model

During drying, wood undergoes "drying strain." The mechanics of wood drying strain potentially involves about four components of strain:

$$\epsilon_{total} = \epsilon_{mechanical} + \epsilon_{shrinkage} + \epsilon_{creep} + \epsilon_{mechanosorptive}, \quad (1)$$

where mechanical strain represents strains assumed to occur instantaneously as load is applied. Shrinkage strains are a function of shrinkage coefficients and moisture change and are also assumed to occur instantaneously with moisture change. Creep strains are time dependent deformations associated with sustained loads. Mechanosorptive strains are a result of an interdependency between strains and stresses induced during moisture change. Differential shrinkages associated with warp can cause all four types of strain to occur within a board.

Although dimensional instability problems associated with crook have been studied over the years, the most significant recent advances and largest technical effort appear to have been undertaken at Lund University in Sweden by Omarsson and others (Omarsson, S., A Finite Element Study of the Shape Stability of Sawn Timber Subjected to Moisture Variations, thesis, Division of Structural Mechanics, Lund Institute of Technology, Lund, Sweden (1995)). Among their advances was the development of a three-dimensional FEM built within the commercial program ABAQUS (Hibbitt, Karlsson & Sorenson, Inc., ABAQUS v. 5.4 (1994), Pawtucket, R I) that included strain rates as shown in Eq. 2:

$$\epsilon_{total} = \epsilon_{mechanical} + \epsilon_{shrinkage} + \epsilon_{mechanosorptive}, \quad (2)$$

The model was designed to simulate dimensional instability through the kiln-drying process. Moisture transport was computed using a two-dimensional linear diffusion model. Elastic material properties and shrinkage coefficients were computed and assigned to the finite element mesh using empirical relationships based on radial distance from the pith. Grain angles were included in the model to simulate a uniform spiral grain. Verification of the determined warp potentials was limited to a favorable comparison with the measured warp patterns of seven 10-mm by 10-mm by 30-mm spruce specimens with different end-ring configurations. The model predictions tended to follow warp profiles suggested by intuition.

In contrast, the objectives of the study leading to the present invention were pursued with exploratory testing programs, development of a stand-alone three-dimensional finite element model (FEM), and analysis of data.

Data used were obtained from a set of nominal 1-inch thick Loblolly pine boards from the Mid-South subjected to post-drying humidity cycles of 20% RH- 23° C. and 90% RH-23° C. environments. These data are referred to as the Stanish Data Set (Stanish, M. Dimensionally Stable Building Materials, WEYERHAEUSER INTERNAL SIGNIFICANT PRESENATION ON PROJECT 042–1041 (1994), Weyerhaeuser Technology Center, Tacoma, Wash.). Warp profiles were recorded as the boards were cycled from one condition to another.

Another data set consisted of bending modulus of elasticity (MOE), ultrasound, and lengthwise shrinkage rates measured from small clear-cut samples of Loblolly Pine taken from 40 trees covering 8 different regions in the South. This data set will be referred to as the Huang Data Set (Huang, C. L., Regional Wood Quality Differences of Loblolly Pine Plantations, WEYERHAEUSER INTERNAL TECHNICAL REPORT, Weyerhaeuser Technology Center, Tacoma, Wash.).

The FEM of the present invention is a three-dimensional model utilizing 20-node isoparametric elements with orthotropic material properties referred to as DIMENS. The DIMENS model is a linear, elastic model with no time dependent strains and with total strain initially computed as shown in Eq. 3:

$$\epsilon_{total} = \epsilon_{mechanical} + \epsilon_{shrinkage}. \quad (3)$$

This approach was chosen because the Stanish data set showed that warp profiles tend to repeat in shape and magnitude through repeated moisture cycles, suggesting that creep and mechanosorptive effects were not predominant for these conditions. Additionally, DIMENS provided a computationally simpler model. These assumptions are not intended to suggest that creep and mechanosorptive effects can be ignored in all warp situations. However, in accordance with a preferred embodiment of the present invention, creep and mechanosorptive effects can be ignored while still accurately determining crook potential. The model included and ignored factors as shown in Table 2.

TABLE 2

Factors included and ignored in the DIMENS model

| Factors Included | Factors Ignored |
| --- | --- |
| Mechanical property variations element by element - primarily E | Time dependent effects such as creep |
| Grain angle variations | Different drying conditions |
| Uniform MC changes | Temperature effects |
| Steady state shrinkage | Variation of shrinkage rate with MC |

Lengthwise shrinkage rates are assumed to be constant over a wide range of moisture contents. As shown in FIG. 6, this assumption is an approximation. Lengthwise shrinkage rates from green to 15% EMC are much lower than lengthwise shrinkage rates from 8% to oven dry. This difference can be taken into account when using DIMENS to predict crook.

A mathematically correct model is established by comparison with a series of closed-form solutions. The most significant aspect of DIMENS model development was to establish a method of assigning elastic and shrinkage properties to each finite element reflecting those properties in the actual board under consideration. Each finite element requires the assignment of, modulus of elasticity in the L, R, T material directions (3 E values), shear modulus in the LR, LT, RT planes (3 G values), Poisson's ratios in the LR, LT, RT planes (3 v values), shrinkage rates in the L, R, T, LR, LT, RT directions (6 SR values), fiber direction angles (2 values, surface and dive) and distance from the pith to establish the ring angle.

To simplify data needs, typical property values for Loblolly pine were used for analysis except $E_L$, $SR_L$, and the 2 fiber direction angles as shown in Table 3.

TABLE 3

Material Input Properties for Finite Element Analysis

| Property | Value | Source (see reference section for complete citation) |
| --- | --- | --- |
| $E_L$ | Measured MOE from bending test for specimen | Measurement |
| $E_R$, $E_T$ | 145,000 psi and 95,000 psi | Bodig and Goodman |
| $G_{LR}$, $G_{LT}$, $G_{RT}$ | 120,000 psi, 110,000 psi, 130,000 psi | Bodig and Goodman |
| $v_R$, $v_{LT}$, $v_{RT}$ | 0.13, 0.27, 0.35 | Green and Kretschmann and Bodig and Goodman |
| $SR_L$ | Measured lengthwise shrinkage rate or predicted from distance from pith | Measurement |
| $SR_R$, $SR_T$ | $-495* SR_L^2 + .139* SR_L + .00179$ $-600* SR_L^2 + .207* SR_L + .00259$ | Based on work by Meylan |
| $SR_{LR}$, $SR_{LT}$, $SR_{RT}$ | 0, 0, 0 | assumption as employed by Omarsson |
| angles, distance from pith | measured for particular board under consideration | measurements |

$SR_{LR}$, $SR_{LT}$ and $SR_{RT}$ were set to zero, and $SR_R$ and $SR_T$ were adjusted according to the value of $SR_L$ based on work by Meylan, B. A, Cause of High Longitudinal Shrinkage in Wood, FOREST PRODUCTS JOURNAL, 18(4): 75–78 (1968). The research effort focused on methods to predict $E_L$ (modulus of elasticity in the longitudinal material direction) and $SR_L$ (shrinkage rate in the longitudinal material direction), and measurement of the fiber direction (grain) angles.

Three possibilities were initially present for predicting lengthwise shrinkage rates: fibril angle, ring number from pith, and modulus of elasticity. Although the literature shows fibril angle to be highly correlated with lengthwise shrinkage rate (see Ying, et al.) the impracticality in measuring it in a production environment removed it from serious consideration.

Investigators at Lund University used ring number from the pith as a predictor for longitudinal shrinkage (Ormarsson, et al., Influence of Annual Ring Orientation on Shape Stability of Sawn Timber, in QUALITY WOOD DRYING THROUGH PROCESS MODELING AND NOVEL TECHNOLOGIES, PROCEEDINGS OF THE 5$^{TH}$ INTERNATIONAL IUFRP WOOD DRYING CONFERENCE (1996), 427436). Data from the USDA FS Forest Products Lab (Ying, et al.) and Weyerhaeuser (Megraw, R. A., WOOD QUALITY FACTORS IN LOBLOLLY PINE, TAPPI Press, Atlanta, Ga. (1985)) are shown in FIGS. 6–7. It is clear from FIG. 7 (FPL Data), that lengthwise shrinkage rates for Loblolly pine cannot be solely a function of ring from pith as it also shows a high dependency on height in stem. FIG. 7 also shows lengthwise shrinkage rates measured from the Huang data set. While the trends shown in FIG. 7 may be present, considerable variability suggests that ring from pith and height in stem are not adequate predictors of lengthwise shrinkage rate.

Figure 20:
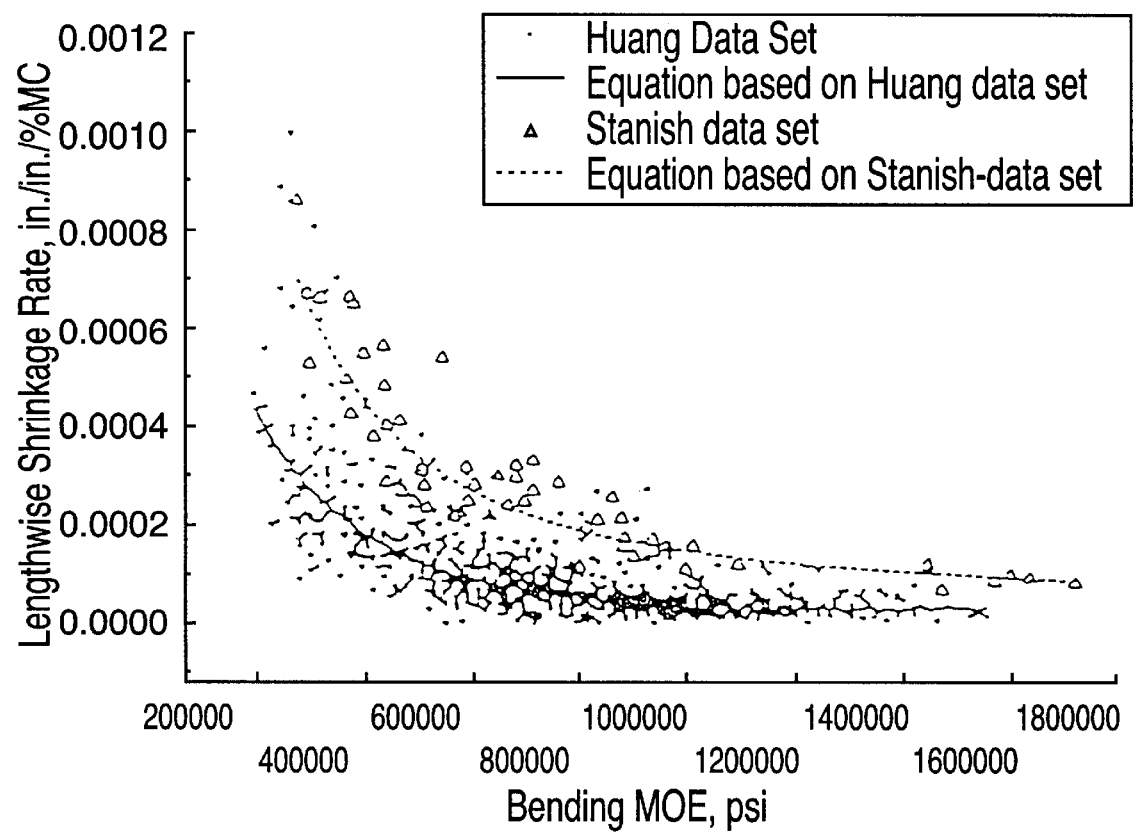
FIG. 20 illustrates data and equations relating bending MOE and longitudinal shrinkage rate for two data sets
Figure 21:
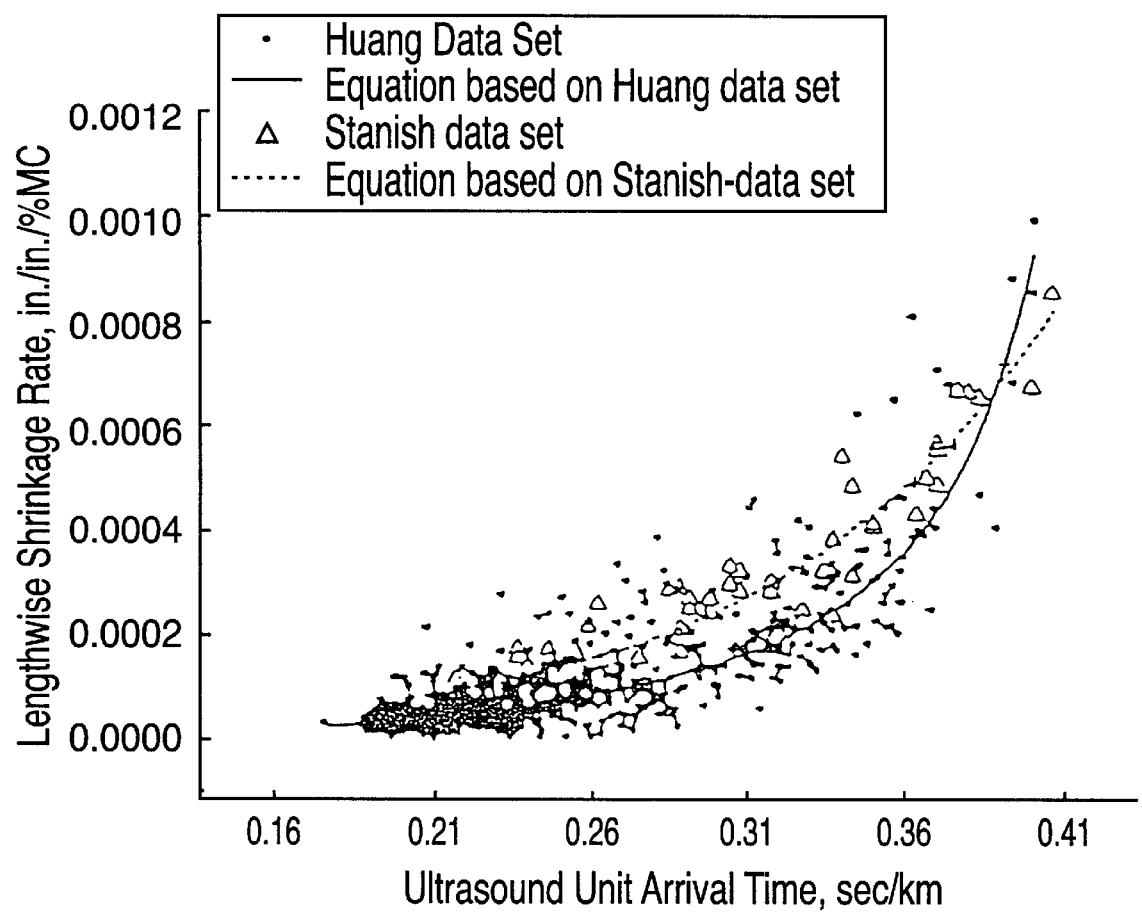
FIG. 21 illustrates data and equations relating ultrasound unit time and lengthwise shrinkage rate for two data sets.

Among the factors of specific gravity, rings per inch, ring from pith, height in stem, and lengthwise modulus of elasticity (MOE), the latter was initially found to provide the strongest relationship with lengthwise shrinkage rates. FIG. 20 shows the relationship observed in the Huang and Stanish data sets. Lengthwise shrinkage rate can vary by more than an order of magnitude with the highest shrinkage rates occurring only in samples with MOE values near the minimum (less than 600,000 psi). FIG. 21 shows the correlation, observed in the Huang and Stanish data sets, between ultrasound unit time and lengthwise shrinkage rates, thus emphasizing again the fact that lengthwise shrinkage rates can be accurately determined from ultrasound velocities.

In some studies, Huang measured ultrasound velocity when the specimens were green and again after they were air dried to a uniform moisture content ranging from 12 to 15%. FIGS. 18–19 show the relationship between ultrasound velocity (km/sec) and lengthwise shrinkage rate for green and dry states respectively. The similarities between FIGS. 18 and 19 show that ultrasound velocity measured either when the wood is green or dry are equally effective in determining lengthwise shrinkage rates.

Figure 22:
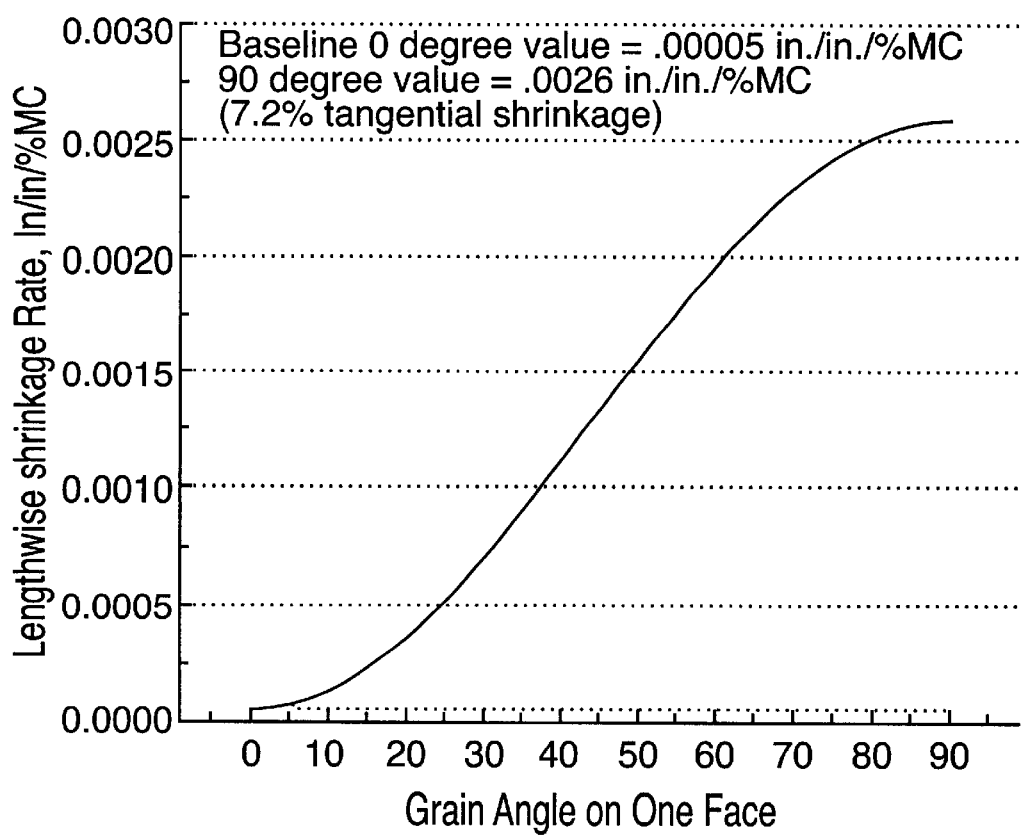
FIG. 22 illustrates the effect of grain angle on lengthwise shrinkage rate based on tensor transformation.

Stresses and strains, including shrinkage induced strains, are second-order Cartesian tensors and thus are assumed to obey the laws of tensor transformation. Therefore, the effect of grain angle on apparent lengthwise shrinkage rates can be computed. As grain angle increases, radial and/or tangential components of shrinkage contribute and dramatically increase the observed lengthwise shrinkage rate. FIG. 22 shows this computed effect on lengthwise shrinkage rates for grain angles in the longitudinal-tangential plane.

Note that the range of measured lengthwise shrinkage rates from the Huang data set cover the same range of values observed for grain angles from 0 to 35 degrees. Because of this anticipated strong influence of grain angle, grain angle measurements were sought as an input to the DIMENS model.

To aid development of the DIMENS model, 8 Loblolly pine boards from the Stanish data set were taken to obtain a more detailed set of measurements. All samples consisted of nominal 1-inch by 6-inch by 8 ft. boards with all containing one or more knots. The warp characteristics of these 8 boards were identified as three with high crook, two with high twist, and three that were straight.

A 36-inch high crook region in each board was identified and cut into nine 1.5-in. by 12-in. specimens. Modulus of elasticity, ultrasound (Sylvatest, 14 kHz), and length were measured at an MC of approximately 5% for each 12-in. specimen. Length changes were recorded as the specimens were cycled from 20% RH to 90% at 23° C. To capture the overall trend in grain angle with a minimum of measurements, laser grain angle measurements were gathered every 7 inches. The laser scanner provided both in-plane surface and out-of-plane surface (dive) angle readings, something the other techniques could not provide. Patches of 9 readings were taken to capture and smooth the localized variation in grain angle.

The DIMENS model and test results were used to conduct four types of analyses to determine crook potentials in a set of specific boards from the Stanish data set. The four types of analyses distinguish different methods for assigning material properties to the each finite element as follows.

Type 1 Assign element $E_L$ based on ring from pith and measured full-length board MOE, predict element longitudinal shrinkage rate ($SR_L$) from element $E_L$, assign measured grain angles to corresponding finite elements.

Type 2 Assign $E_L$ and longitudinal shrinkage rate ($SR_L$) to the corresponding element based on measurements of MOE and lengthwise shrinkage rate (LSR), respectively, from nine 1.5-in by 12-in specimens cut from a high warp 36-inch section of the subject board, assign all grain angles as 0.0.

Type 3 Assign $E_L$ based on the measured MOE from the small specimens and assign $SR_L$ based on the LSR predicted from MOE, assign all grain angles as 0.0.

Type 4 Assign $E_L$ to each finite element based on the average board MOE and use ultrasound measurements to predict a corresponding value of LSR, assign the LSR's to the finite element SRL's with all grain angles assigned as 0.0.

Analyses were conducted on 36-inch samples of high warp boards from the Stanish data set (except where noted). Each board sample was separated into 12 elements across the 5.5-inch width, 1 element through the 0.75-inch thickness, and 12 elements along the 36-inch length for a total of 144 elements. Grain angles were set to zero in Analysis Types 2 through 4 since it was believed that the influence of grain angles was captured in measurements of lengthwise shrinkage rates.

Analysis Type 1 followed the logic employed at Lund University where element properties and shrinkage assignments were dependent on ring from pith. Results from analysis Type 1 did not accurately determine crook potential proving that location within log and averaged log property and shrinkage characteristics are insufficient warp prediction parameters. Ring from pith proved to be an unreliable predictor of MOE and lengthwise shrinkage rate gradients were not accurately predicted, resulting in consistently inaccurate determination of crook potentials.

Analysis Type 2 successfully determined crook potential based on measured MOE's and measured lengthwise shrinkage rates assigned to the finite elements. FIGS. 8–10 show the actual measured crook potential and computed crook for three high crook boards. The actual crook shown in these figures consists of the difference between the board shapes at 90% RH and 20% RH after two cycles of moisture exposure. Two straight boards (specimens 19–51a and 2–52c (profiles not shown)) were also analyzed by the same procedure. Determined crook potentials were essentially straight and compared favorably with the actual measured crooks.

Analyses type 3 and 4 were directed at identifing methods to predict lengthwise shrinkage rate gradients within boards via indirect, nondestructive measurements. MOE and ultrasound measurements were explored as predictors of lengthwise shrinkage rates for 12-inch samples cut from 8 boards from the Stanish data set. Equations were fit to these data and those obtained from the Huang data set.

FIG. 20 shows the data and resulting equations. Again, lengthwise shrinkage rates are plotted as grain angles, knots and other growth defects within the 1.5-in by 12-in beams make direct measurement of true longitudinal shrinkage impossible. The best fit to the Huang and Stanish data sets are the following equations 4 and 5:

$$LSR_{Huang} = 0.00267 e^{(-6.349 \times 10^{-6} MOE + 2.212 \times 10^{-12} MOE^2)}, \quad (4)$$

and $$LSR_{Stanish} = 0.00804 e^{(-8.500 \times 10^{-6} MOE + 7.084 \times 10^{-12} MOE^2 - 2.959 \times 10^{-18} MOE^3 + 4.828 \times 10^{-25} MOE^4)}, \quad (5)$$

where LSR=Lengthwise shrinkage rate (in./in./% MC), and MOE=Modulus of Elasticity (psi) measured from a bending test.

The Huang and Stanish data sets are each based on Loblolly pine, but each set of data was gathered at different moisture content (5% vs. 12%). The moisture content difference may explain the difference in the equations.

Similarly, equations were fit to ultrasound and lengthwise shrinkage rate measurements as shown in FIG. 21. The best fit equations are equations 6, 7 and 8. Again, the data sets yield two different equations. In this case, the ultrasound measurements for the Stanish data set were measured at approximately 20% MC and the Huang data set was measured in the range of 12 to 15%. The ultrasound unit arrival times would change by approximately 5% to bring the values to a common moisture content. Equations 6, 7 and 8 are as follows:

$$LSR_{Huang} = 3.059 \times 10^{-4} e^{(-7.650 \times 10^{-4} Utime_{12\%} + 57.80 Utime_{12\%}^2 - 157.1 Utime_{12\%}^3 + 1552.5 Utime_{12\%}^4)}, \quad (6)$$

$$LSR_{Stanish} = 9.43 \times 10^{-6} e^{(10.4 Utime_{20\%})}, \quad (7)$$

and $$LSR_{Stanish} = 7.681 \times 10^{-6} e^{(11.5.4 Utime_{12\%})}, \quad (8)$$

where LSR=lengthwise shrinkage rate (in./in./% MC) and Utime=unit ultrasound arrival time (sec./km) each measured on 12-in samples at the approximate moisture content indicated.

Equations 5, 7 and 8 representing the Stanish data set were used to predict lengthwise shrinkage rates based on measurements of MOE or unit ultrasound arrival time for the three high crook profile boards. These predicted lengthwise shrinkage rates were assigned to corresponding finite elements, and Type 3 and 4 analyses were performed. FIGS. 8–10 show the determined crook potential and the actual measured crook profiles.

Based on the three comparisons in FIGS. 8–10, ultrasonic unit arrival time is as good or better than MOE as a predictor of lengthwise shrinkage rate.

The sensitivities of assigned MOE and grain angle on predicted crook profiles were considered through a series of DIMENS simulations. Except as a predictor of lengthwise shrinkage rate, the DIMENS model showed little sensitivity to changes in the MOE.

Figure 23:
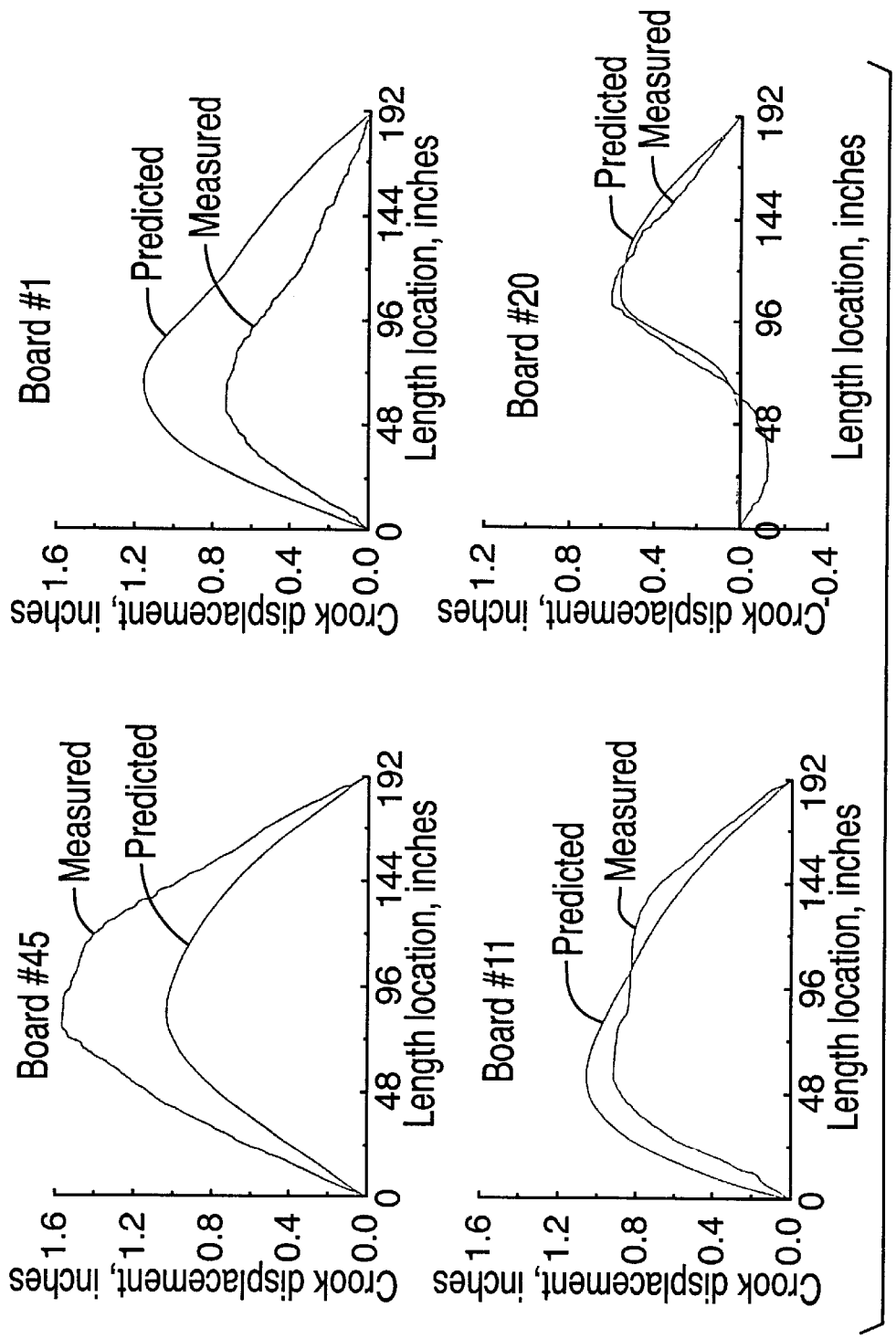
FIG. 23 illustrates the accuracy of determined crook potentials for 2×4 inch plantation wood samples.
Figure 24:
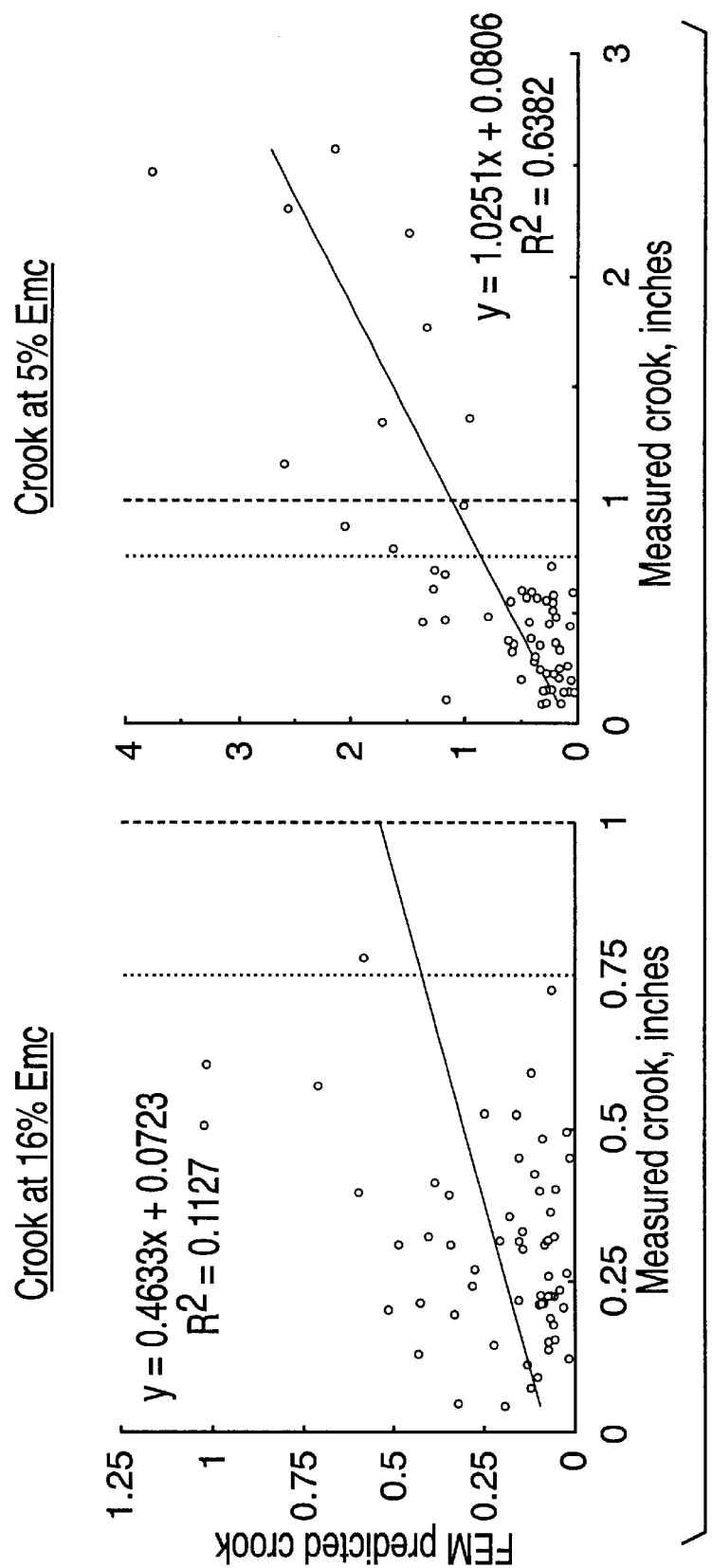
FIG. 24 illustrates the accuracy of determined crook potentials for 2×4 inch hemlock samples at different moisture contents.

Based on the results presented above, ultrasound unit arrival time is a viable technique for detecting differential lengthwise shrinkage rates and providing a basis for determining crook potentials with the DIMENS model. Ultrasound velocity patterns were measured on green 16-ft. 2×4's. These were converted to lengthwise shrinkage rates, which were used in the DIMENS model to predict crook potential for each piece. In each case, modulus of elasticity was set to a uniform 800,000 psi throughout the simulated board, grain angles were set to 0.0 and lengthwise shrinkage rates were predicted based on ultrasound measurements. In these additional analyses, ultrasound readings were gathered in-situ without cutting the boards. A comparison of measured and predicted warp profiles for the boards, as seen in FIG. 23, showed that the DIMENS model correctly determined crook potential.

Therefore, ultrasound measurements can be used to determine crook potential in lumber. From these predictions, decisions can be made concerning how to process and use the lumber. For example, lumber with a predicted crook in excess of a threshold can be processed using special drying techniques and then sold for use in environments having relatively constant moisture or for warp insensitive applications. Lumber or logs with a higher predicted crook likewise can be separated for particular cases.

Figure 25:
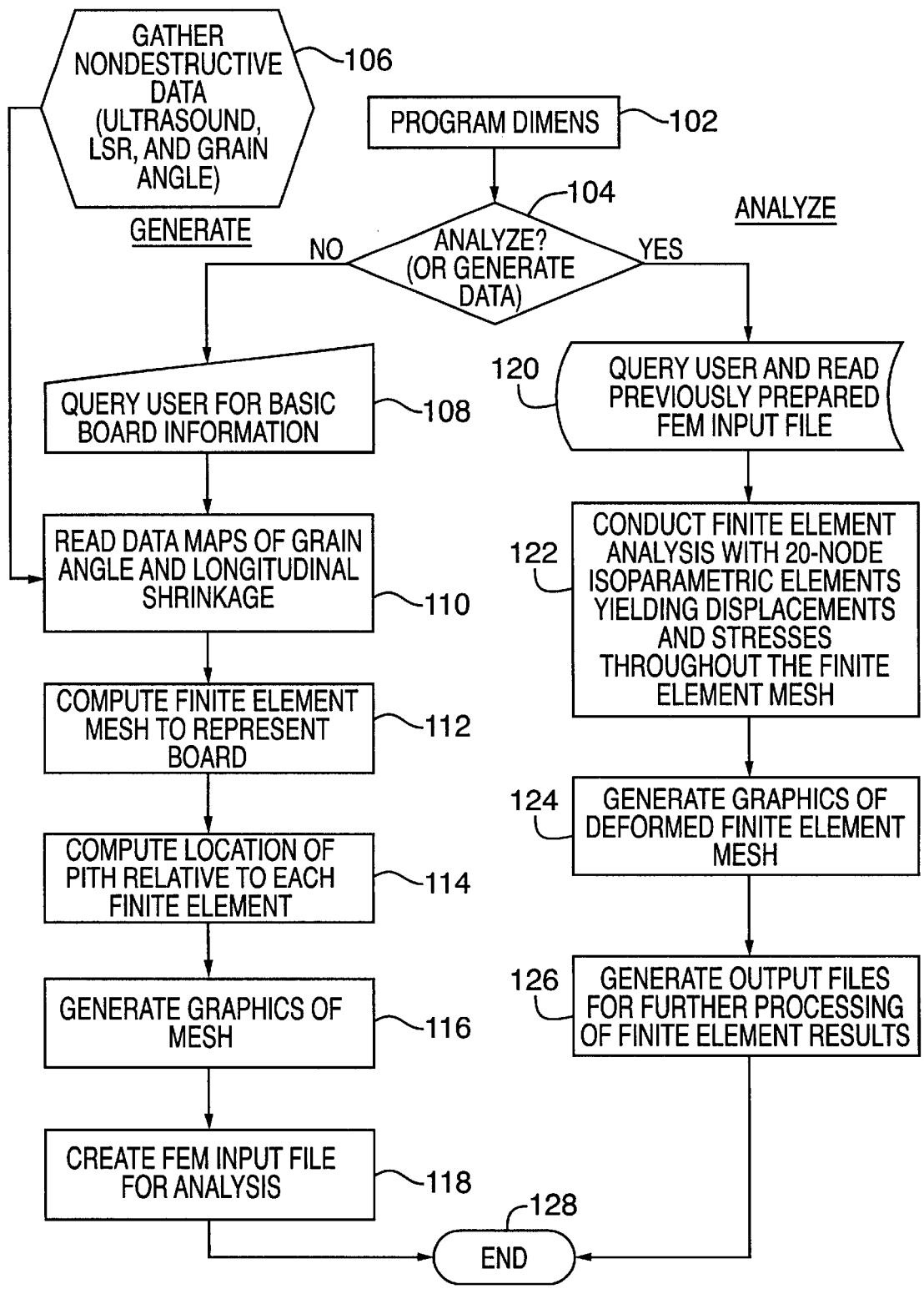
FIG. 25 portrays the DIMENS program as a functional flow-chart.

FIG. 25 is a flowchart of a method used according to the DIMENS model. While it is possible to compute the DIMENS model by hand or using a calculator, the model is usually embodied in the form of a computer program (102). For example, working embodiments of the present invention use a DIMENS model written in the FORTRAN programming language, compiled, and executed on a commercially available personal computer running the Microsoft® Windows 95 operating system. Alternative embodiments of the computerized DIMENS model are possible, such as models written in different programming languages or compiled programs running on different computers running different operating systems. One embodiment of the DIMENS computer program is listed in Appendix A.

The DIMENS model offers the choice (104) of analyzing an already existing FEM input file, or generating an FEM input file from independent measurements such as lengthwise shrinkage rates and grain angles obtained from ultrasound measurements. If the user chooses to analyze data, the user supplies an existing FEM input file, such as a file previously generated by the user or someone else. If the user chooses to generate data, two options are available to the user. First, the user may supply the data independently, such as from a separate source file (106). Second, the can be queried for basic board information (108).

In many embodiments, the user of the DIMENS program begins with an independent database of lengthwise shrinkage rates (and possibly other measurements) gathered from a particular piece of wood. The user may supply this data (106), such as ultrasound measurements, which is converted and read as data maps of grain angle and longitudinal shrinkage rates (110). Alternatively, the DIMENS program may prompt the user for this basic board information (108). Once the data maps of grain angle and longitudinal shrinkage rate are read, the model computes a finite element mesh to represent the board (112). Note that the grain angle can be set to zero in this model. The model then computes the pith relative to the location of each finite element (112). In lumber, the location of the pith is determined according to ring number. Finally, the model generates a graphic representation of the finite element mesh (116) and creates an FEM input file for analysis (118). At this point, the user has finished using the DIMENS model to generate the FEM input file (128). However, the user has the option to—at that moment or any time later—use the FEM input file as a source file for further analysis under the DIMENS model (104).

If the user chooses to continue further analysis (104), the DIMENS program asks the user for a previously generated FEM input file (120), such as the file the user just generated. Alternatively, the user may designate any suitable FEM input file generated previously, such as an FEM input file generated by another DIMENS program running on a different computer in a different location.

After the FEM input file is designated as the source file for further analysis, the program conducts an FEM analysis to compute displacements and stresses throughout the finite element mesh (122). The analysis is based on 20-node isoparametric elements yielding displacements and stresses through the finite element mesh (122). Based on these computed displacements and stresses, a graphic representation of the deformed finite element mesh is generated (124), which comprises a quantitative determination of crook potential, such as the graphic representation seen in FIG. 2. Finally, output files for further processing of finite element results are generated (126) and the program ends (128).

Example #3
Using Infrared Radiation to Measure Lengthwise Shrinkage Rates

Infrared (IR) energy may be used in addition to or in place of other indirect measurement methods, such as ultrasound energy, in measuring lengthwise shrinkage rates. FIG. 4 shows the relationship between lengthwise shrinkage rates and actual measured shrinkage. The relationship between lengthwise shrinkage rates and IR measurements exhibits a nonlinear characteristic similar to that of the relationship between lengthwise shrinkage rates and ultrasound measurements (see FIG. 17). These IR measurements were obtained by IR spectroscopy analysis, and predicted lengthwise shrinkage rates were determined by a PLS statistical model derived from the IR spectra.

Example #4
Comparison with Previous Methods

As stated above, Kliger et al. teaches a destructive method for measuring longitudinal shrinkage and approximate method for modeling crook. FIGS. 8–10 illustrate a comparison between the method of Kliger et al. (edge calculation) and the method of the present invention (strain model) for particular boards. As can be readily seen in these figures, the method of the present invention demonstrates a superior method for determining crook potential compared to the method of Kliger et al.

To determine crook potential using the method of the present invention, a procedure essentially similar to that of Example #2 was followed. To determine the edge calculation of the method of Kliger et al., an average lengthwise shrinkage rate for each of the two edges was determined. The radius of curvature was calculated using the two averaged LSR's and geometric analysis. Crook for the given board length was calculated using the radius of curvature.

In all boards, the method of the present invention determined a crook potential that more closely matched actual measured crook. In boards exhibiting a high amount of crook, the crook potential determined using the present method provided much better correlation to actual measured crook than the Kliger et al. method. For example, board 54–14A of FIG. 9 demonstrated highly variable crook along the length of the board, exhibiting both positive and negative crook displacement. The present method determined a crook potential closely correlated to the actual measured crook, while the method of Kliger et al. incorrectly predicted a negative crook displacement along the entire length of the board.

In another example, board 54–16A of FIG. 8 demonstrated high crook displacement and a declining magnitude of crook displacement along the length of the board. The present method determined a crook potential that, when plotted, closely matched the curve of the plotted actual crook displacement. The Kliger et al. method, however, did not correctly predict the same pattern of magnitude in actual crook displacement.

Example #5
Standing Timber and Harvested Logs

This example describes a method that can be used to practice the present invention on standing trees. Acoustic measurements are made around the perimeter of a standing tree at a measuring location, or locations, such as at substantially 4-foot intervals along the long axis of the tree. These acoustic measurements are then used to determine warp potential of the wood as discussed herein.

Alternatively, core samples can be taken from a standing tree. Measurements, such as acoustic energy measurements, are then made along the diameter of the core in the direction of the trachiads. These measurements are then used to determine warp potential as described herein.

Having illustrated and described the principles of our invention with reference to several specific examples, it should be apparent that these examples may be varied in arrangement and detail without departing from these principles. All such variations fall within the scope of the following claims.

We claim:

1. A method for determining crook potential of wood, comprising:
    nondestructively obtaining a lengthwise shrinkage rate of wood at a measuring location along the wood; and
    determining crook potential of the wood based on the lengthwise shrinkage rate.

2. The method according to claim 1 where obtaining a lengthwise shrinkage rate comprises determining a lengthwise shrinking rate from a measurement obtained by a nondestructive method selected from the group consisting of electromagnetic radiation, acoustic energy, and combinations thereof.

3. The method according to claim 2 where the acoustic energy is ultrasound.

4. The method according to claim 2 where the lengthwise shrinkage rate is determined using infrared radiation.

5. The method according to claim 2 where the lengthwise shrinkage rate is determined using ultrasound.

6. The method according to claim 5 where the lengthwise shrinkage rate is determined by:
    sending an ultrasound pulse through the wood; and
    measuring the transmission speed of the ultrasound pulse through the wood.

7. The method according to claim 6 where the lengthwise shrinkage rate is determined using an empirically derived formula.

8. The method according to claim 7 where the lengthwise shrinkage rate is determined using the formula $LSR = 9.43 \times 10^{-6} e^{(10.4 Utime_{20\%})}$ where LSR is the lengthwise shrinkage rate, and Utime is a unit time measurement of speed over a given distance at 20 percent moisture content of the wood.

9. The method according to claim 7 where the lengthwise shrinkage rate is determined using the formula: $LSR = 7.681 \times 10^{-7} e^{(11.54 Utime_{12\%})}$ where LSR is the lengthwise shrinkage rate, and Utime is a unit time measurement of speed over a given distance at 12 percent moisture content of the wood.

10. The method according to claim 6 where the lengthwise shrinkage rate is determined by sending plural ultrasound pulses through the wood.

11. The method according to claim 6 where plural lengthwise shrinkage rates are determined by sending plural ultrasound pulses through the wood.

12. The method according to claim 1 where the wood is lumber.

13. The method according to claim 12 where the lumber comprises a board having major planar surfaces.

14. The method according to claim 13 where plural measuring locations are located on at least one major planar surface.

15. The method according to claim 14 where at least two measuring locations are separated by a predetermined distance.

16. The method according to claim 14 where each measurement is made at substantially one-foot intervals along the board.

17. The method according to claim 1 further comprising obtaining plural lengthwise shrinkage rates at plural measuring locations.

18. The method according to claim 17 where obtaining lengthwise shrinkage rates comprises determining the lengthwise shrinkage rate at each of the plural measuring locations.

19. The method according to claim 17 where obtaining lengthwise shrinkage rates comprises determining the lengthwise shrinkage rate at at least one of the plural measuring locations.

20. The method according to claim 1 where obtaining a lengthwise shrinkage rate comprises determining a lengthwise shrinkage rate using an algorithm.

21. The method of claim 20 where the algorithm relates modulus of elasticity to the lengthwise shrinkage rate.

22. The method according to claim 21 where the lengthwise shrinkage rate is determined using the formula $LSR = 0.00267 e^{(-8.500 \times 10^{-6} MOE + 7.084 \times 10^{-12} MOE_2 - 2.959 \times 10^{-18} MOE_3 + 4.828 \times 10^{-25} MOE_4)}$, where LSR is the lengthwise shrinkage rate and MOE is the modulus of elasticity.

23. The method according to claim 1 where determining crook potential is done by a computer.

24. The method according to claim 1 where crook potential correlates to bow potential.

25. The method according to claim 1 where obtaining a lengthwise shrinkage rate comprises measuring a lengthwise shrinkage rate.

26. A method for determining crook potential, comprising:
   indirectly obtaining a lengthwise shrinkage rate of wood by energy propagation at a measuring location along the wood; and
   determining crook potential of the wood based on the lengthwise shrinkage rate.

27. The method according to claim 26 further comprising obtaining plural lengthwise shrinkage rates at plural measuring locations.

28. The method according to claim 26 where obtaining the lengthwise shrinkage rate comprises obtaining modulus of elasticity of the wood at the measuring location.

29. The method according to claim 28 where modulus of elasticity is determined using acoustic energy.

30. The method according to claim 29 where the acoustic energy is ultrasound.

31. The method according to claim 26 where obtaining the lengthwise shrinkage rate comprises obtaining chemical information of the wood at the location.

32. The method according to claim 31 where the lengthwise shrinkage rate is determined spectroscopically.

33. The method according to claim 32 where the lengthwise shrinkage rate is determined using infrared spectroscopy.

34. The method according to claim 33 and further comprising determining plural lengthwise shrinkage rates using both ultrasound and infrared spectroscopy.

35. A method for determining crook potential in wood, comprising:
   providing a wood piece having a major long axis;
   setting an arbitrary zero plane substantially parallel to the long axis of the wood piece;
   measuring lengthwise shrinkage rates along an axis substantially parallel to the zero plane; and
   determining crook potential from the lengthwise shrinkage rates, the crook potential being correlated to the actual crook of the wood by a linear $R^2$ of greater than 0.5 at a moisture content of 12% or less.

36. The method according to claim 35 where the $R^2$ value is greater than 0.6 at a moisture content of 12% or less.

37. The method according to claim 35 where lengthwise shrinkage rates are determined indirectly.

38. The method according to claim 37 where the lengthwise shrinkage rates are determined using a method selected from the group consisting of infrared radiation, microwave radiation, electricity, acoustic energy, and combinations thereof.

39. The method according to claim 38 where lengthwise shrinkage rates are determined by measuring ultrasound transmission speeds through the work piece.

40. A method for determining crook potential in wood, comprising:
   providing a piece of wood having at least one major planar surface;
   positioning the piece of wood adjacent to a device for collecting energy from the piece of wood to determine at least one lengthwise shrinkage rate; and
   determining the crook potential of the piece of wood from the at least one lengthwise shrinkage rate.

41. The method according to claim 40 where the piece of wood comprises lumber.

42. The method according to claim 40 where the energy is selected from the group consisting of ultrasound, infrared radiation, microwave radiation, electricity, and combinations thereof.

43. The method according to claim 42 where the energy is ultrasound.

44. The method according to claim 43 where the device has first and second elements, the ultrasound passing from the first element through the wood to the second element.

45. The method according to claim 40 where two or more lengthwise shrinkage rates are determined.

46. The method according to claim 45 where each lengthwise shrinkage rate is determined at a measuring location.

47. The method according to claim 46 where measuring locations are located on at least one major planar surface of the wood.

48. The method according to claim 46 where measuring locations are located at regularly spaced intervals along the wood.

49. The method according to claim 40 where the crook potential is determined using a computer.

50. The method according to claim 40 where the method for determining lengthwise shrinkage rate is nondestructive.

51. A method for determining crook potential of wood, comprising:
   obtaining lengthwise shrinkage rates of wood at plural measuring locations along the wood; and
   determining crook potential of the wood based on non-averaged lengthwise shrinkage rates.

52. The method according to claim 51 where obtaining lengthwise shrinkage rates comprises determining the lengthwise shrinkage rates indirectly.

53. The method according to claim 52 where lengthwise shrinkage rates are determined nondestructively.

54. The method according to claim 51 where crook potential is determined using a finite element model.

55. The method according to claim 51 where the crook potential is determined using the DIMENS model.

56. A method for cultivating, harvesting and processing trees, comprising:
   nondestructively determining crook potential of trees; and
   cultivating, harvesting and processing trees based upon the determined crook potential.

57. The method according to claim 56 where processing trees comprises determining how to saw an individual tree based on crook potential.

58. A method for determining crook potential, comprising:

making at least one energy measurement;

correlating the at least one energy measurement with at least one lengthwise shrinkage rate; and determining crook potential from the at least one lengthwise shrinkage rate.

59. A method for determining crook potential, comprising:

indirectly obtaining a lengthwise shrinkage rate of wood by determining a modulus of elasticity of the wood; and determining crook potential of the wood based on the lengthwise shrinkage rate.

60. The method according to claim 59 further comprising obtaining plural lengthwise shrinkage rates.

61. The method according to claim 59 where modulus of elasticity is determined using acoustic energy.

62. The method according to claim 61 where the acoustic energy is ultrasound.

63. The method according to claim 59 where obtaining the lengthwise shrinkage rate comprises obtaining chemical information of the wood at the location.

64. The method according to claim 63 where the lengthwise shrinkage rate is determined spectroscopically.

65. The method according to claim 64 where the lengthwise shrinkage rate is determined using infrared spectroscopy.

66. The method according to claim 65 further comprising determining plural lengthwise shrinkage rates using both ultrasound and infrared spectroscopy.

* * * * *